(12) United States Patent
Pulliam et al.

(10) Patent No.: US 12,064,631 B2
(45) Date of Patent: Aug. 20, 2024

(54) ECAP AND POSTURE STATE CONTROL OF ELECTRICAL STIMULATION

(71) Applicant: Medtronic, Inc., Minneapolis, MN (US)

(72) Inventors: Christopher L. Pulliam, Plymouth, MN (US); David A. Dinsmoor, North Oaks, MN (US); Hank Bink, Golden Valley, MN (US); Kristin N. Hageman, Dayton, MN (US)

(73) Assignee: Medtronic, Inc., Minneapolis, MN (US)

( * ) Notice: Subject to any disclaimer, the term of this patent is extended or adjusted under 35 U.S.C. 154(b) by 535 days.

(21) Appl. No.: 17/100,384

(22) Filed: Nov. 20, 2020

(65) Prior Publication Data

US 2021/0187302 A1 Jun. 24, 2021

Related U.S. Application Data

(60) Provisional application No. 62/950,759, filed on Dec. 19, 2019.

(51) Int. Cl.
*A61N 1/36* (2006.01)

(52) U.S. Cl.
CPC ..... *A61N 1/36139* (2013.01); *A61N 1/36062* (2017.08); *A61N 1/36153* (2013.01); *A61N 1/36171* (2013.01); *A61N 1/36175* (2013.01)

(58) Field of Classification Search
CPC .................................................. A61N 1/36139
See application file for complete search history.

(56) References Cited

U.S. PATENT DOCUMENTS 8,515,549 B2    8/2013    Panken et al.
8,958,885 B2    2/2015    Panken et al.
(Continued)

FOREIGN PATENT DOCUMENTS

CN    105792745 A    7/2016
EP    3357533 A1    8/2018
(Continued)

OTHER PUBLICATIONS

International Search Report and Written Opinion of International Application No. PCT/US2020/063690, mailed Apr. 1, 2021, 12 pp.
(Continued)

*Primary Examiner* — Mallika D Fairchild
*Assistant Examiner* — Thien Jason Tran
(74) *Attorney, Agent, or Firm* — Shumaker & Sieffert, P.A.

(57) ABSTRACT

Systems, devices, and techniques for adjusting electrical stimulation based on a posture state of a patient are described. For example, a system may include sensing circuitry configured to sense an ECAP signal and processing circuitry configured to control delivery of the electrical stimulation to a patient according to a first value of a stimulation parameter and determine a characteristic value of the ECAP signal. The processing circuitry may also be configured to receive, from a sensor, a posture state signal representing a posture state of the patient, determine, based on the posture state signal, a gain value for the stimulation parameter, adjust, based on the characteristic value of the ECAP signal and the gain value, the first value of the stimulation parameter to a second value of the stimulation parameter, and control delivery of the electrical stimulation according to the second value of the stimulation parameter.

32 Claims, 9 Drawing Sheets

(56) References Cited

U.S. PATENT DOCUMENTS

| | | |
|---|---|---|
| 9,084,900 B2 | 7/2015 | Hershey et al. |
| 9,302,112 B2 | 4/2016 | Bornzin et al. |
| 9,381,356 B2 | 7/2016 | Parker et al. |
| 9,511,231 B1 | 12/2016 | Kent et al. |
| 9,533,148 B2 | 1/2017 | Carcieri |
| 9,592,387 B2 | 3/2017 | Skelton et al. |
| 10,183,168 B2 | 1/2019 | Baru et al. |
| 10,327,654 B2 | 6/2019 | Strahl et al. |
| 2011/0270134 A1* | 11/2011 | Skelton .............. A61N 1/36514 600/595 |
| 2014/0277282 A1 | 9/2014 | Jaax |
| 2015/0032181 A1 | 1/2015 | Baynham et al. |
| 2015/0173636 A1 | 6/2015 | Mokeke et al. |
| 2015/0360031 A1* | 12/2015 | Bornzin .............. A61N 1/36139 607/62 |
| 2016/0157769 A1 | 6/2016 | Min et al. |
| 2016/0287126 A1 | 10/2016 | Parker et al. |
| 2017/0135624 A1 | 5/2017 | Parker |
| 2017/0361101 A1 | 12/2017 | Single |
| 2018/0126169 A1 | 5/2018 | Hou et al. |
| 2019/0168000 A1* | 6/2019 | Laird-Wah ......... A61N 1/36139 |
| 2019/0175904 A1 | 6/2019 | Baru et al. |

FOREIGN PATENT DOCUMENTS

| | | |
|---|---|---|
| EP | 3024540 B1 | 10/2018 |
| JP | 2018513714 A | 5/2018 |
| WO | 2012155188 A1 | 11/2012 |
| WO | 2015013398 A1 | 1/2015 |
| WO | 2016161484 A2 | 10/2016 |
| WO | 2017100866 A1 | 6/2017 |
| WO | 2017173493 A1 | 10/2017 |
| WO | 2017219096 A1 | 12/2017 |
| WO | 2018053336 A1 | 3/2018 |
| WO | 2019246579 A1 | 12/2019 |
| WO | 2019246582 A1 | 12/2019 |

OTHER PUBLICATIONS

U.S. Appl. No. 17/100,455, filed Nov. 20, 2020, by Pulliam et al.
Schade et al., "Automatic Adaptation of Neurostimulation Therapy in Response to Changes in Patient Position: Results of the Posture Responsive Spinal Cord Stimulation (PRS) Research Study," Pain Physician, vol. 14, No. 5, Sep./Oct. 2011, pp. 407-417.
Office Action from U.S. Appl. No. 17/100,455 dated Jul. 21, 2023, 14 pp.
Notice of Allowance from U.S. Appl. No. 17/100,455 dated Jan. 26, 2024, 9 pp.
Response to Office Action dated Jul. 21, 2023 from U.S. Appl. No. 17/100,455, filed Oct. 23, 2023, 15 pp.
Corrected Notice of Allowance from U.S. Appl. No. 17/100,455 dated May 20, 2024, 2 pp.

* cited by examiner

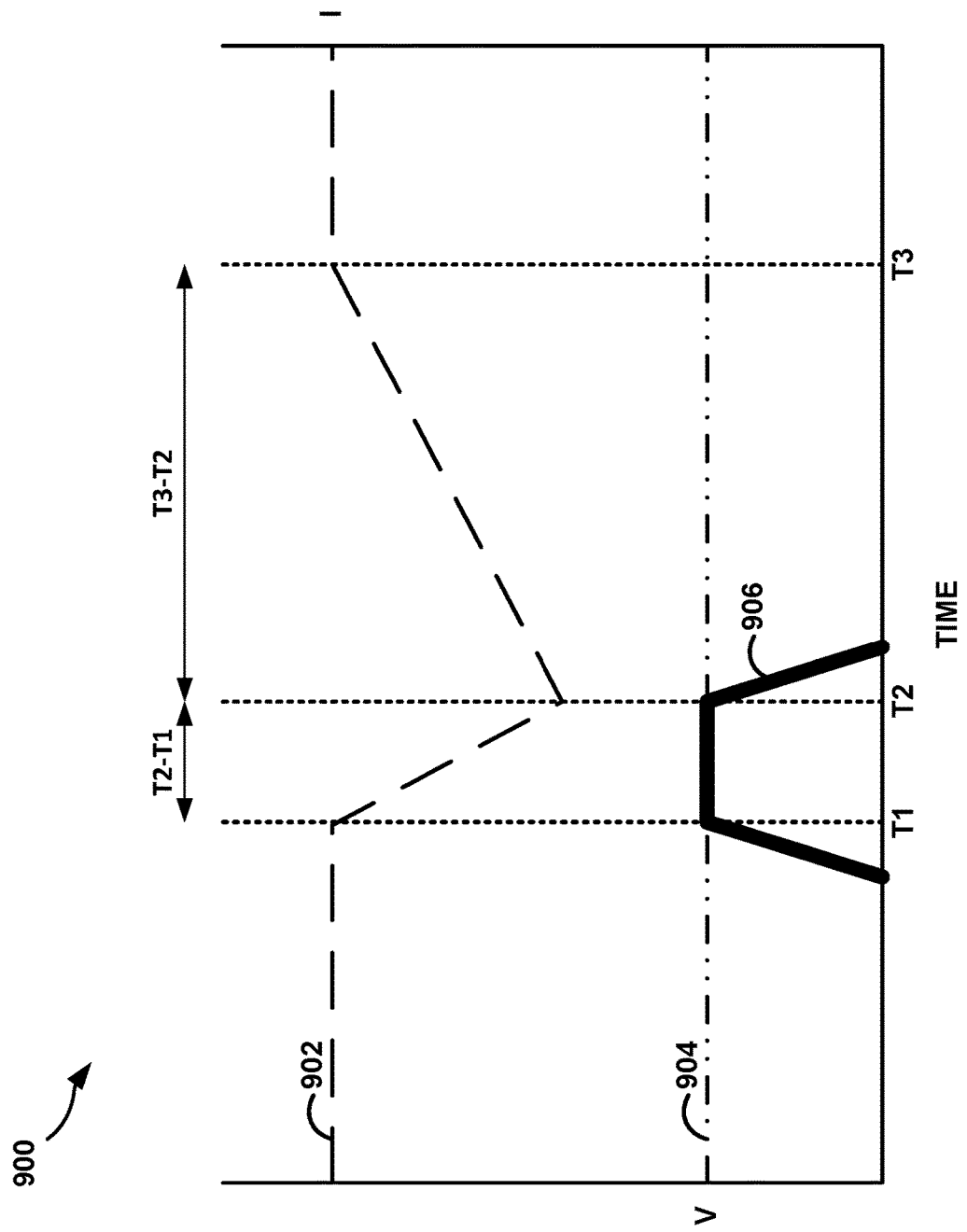

ECAP AND POSTURE STATE CONTROL OF ELECTRICAL STIMULATION

This application claims the benefit of U.S. Provisional Patent Application No. 62/950,759 filed on Dec. 19, 2019, the entire content of which is incorporated herein by reference.

TECHNICAL FIELD

This disclosure generally relates to electrical stimulation, and more specifically, control of electrical stimulation.

BACKGROUND

Medical devices may be external or implanted and may be used to deliver electrical stimulation to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively. Electrical stimulation may be delivered by the medical device as a train of pulses, and the values of the parameters defining the pulses may be altered.

SUMMARY

In general, systems, devices, and techniques are described for managing the delivery of electrical stimulation based on evoked compound action potential (ECAP) signals sensed from a patient. When a patient moves, the distance between implanted electrodes and target nerves changes. For example, electrodes implanted along the spinal column are closer to the spinal cord when a subject lies in a supine posture state as compared to a standing posture state. Similarly, the implanted electrodes may move closer to the spinal cord when a subject coughs or sneezes. This changing distance between the electrodes and target tissue affects neural recruitment for a given intensity of delivered stimulation and can cause the patient's perception and/or therapeutic benefit to also change. Therefore, a characteristic value of the ECAP signal can represent the change in distance, and a system can modulate electrical stimulation using the characteristic value as feedback.

When in different posture states (e.g., sitting as compared to laying in the supine position), the different distances between the electrodes and target tissue cause the patient to have different levels of sensitivity to changes in stimulation parameters that define electrical stimulation. In this manner, a growth curve of the ECAP signal (e.g., the relationship between the characteristic value of the ECAP and amplitude of the stimulation pulse) can depend on at least in part on a posture state of the patient. In one examples, the closer the distance between the electrodes and the target tissue, the greater the sensitivity and slope of the growth curve. As described herein, a system may use detected posture state of the patient to inform how the system uses the ECAP signal in a control policy that defines changes to stimulation parameter values for subsequent pulses, such as a frequency, an amplitude, a pulse width, and a pulse shape. The stimulation pulses may or may not contribute to a therapeutic effect for the patient. In one example, the system may select a gain value associated with a detected posture state for adjusting a stimulation parameter value. The gain value may be associated with the respective growth curve of that detected posture state. In addition, or alternatively, the system may select a target ECAP characteristic value according to the detected posture state of the patient.

In one example, a system includes sensing circuitry configured to sense an evoked compound action potential (ECAP) signal elicited by delivered electrical stimulation and processing circuitry configured to control delivery of the electrical stimulation to a patient according to a first value of a stimulation parameter, determine a characteristic value of the ECAP signal detected from the electrical stimulation, receive, from a sensor, a posture state signal representing a posture state of the patient, determine, based on the posture state signal, a gain value for the stimulation parameter, adjust, based on the characteristic value of the ECAP signal and the gain value, the first value of the stimulation parameter to a second value of the stimulation parameter, and control delivery of the electrical stimulation according to the second value of the stimulation parameter.

In another example, a method includes sensing, via sensing circuitry, an evoked compound action potential (ECAP) signal elicited by delivered electrical stimulation, controlling, by processing circuitry, delivery of the electrical stimulation to a patient according to a first value of a stimulation parameter, determining, by the processing circuitry, a characteristic value of the ECAP signal detected from the electrical stimulation, receiving, by the processing circuitry and from a sensor, a posture state signal representing a posture state of the patient, determining, by the processing circuitry and based on the posture state signal, a gain value for the stimulation parameter, adjusting, by the processing circuitry and based on the characteristic value of the ECAP signal and the gain value, the first value of the stimulation parameter to a second value of the stimulation parameter, and controlling, by the processing circuitry, delivery of the electrical stimulation according to the second value of the stimulation parameter.

In another example, a computer-readable storage medium comprising instructions that, when executed by processing circuitry, cause the processing circuitry to control delivery of the electrical stimulation to a patient according to a first value of a stimulation parameter, receive an evoked compound action potential (ECAP) signal elicited by delivered electrical stimulation, determine a characteristic value of the ECAP signal detected from the electrical stimulation, determine, based on the posture state signal, a gain value for the stimulation parameter, adjust, based on the characteristic value of the ECAP signal and the gain value, the first value of the stimulation parameter to a second value of the stimulation parameter, and control delivery of the electrical stimulation according to the second value of the stimulation parameter.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages of the techniques will be apparent from the description and drawings, and from the claims.

BRIEF DESCRIPTION OF DRAWINGS

FIG. 9 is a graph illustrating a relationship between sensed ECAP voltage amplitude and stimulation current amplitude, in accordance with one or more techniques of this disclosure.

Like reference characters denote like elements throughout the description and figures.

DETAILED DESCRIPTION

Figure 1:
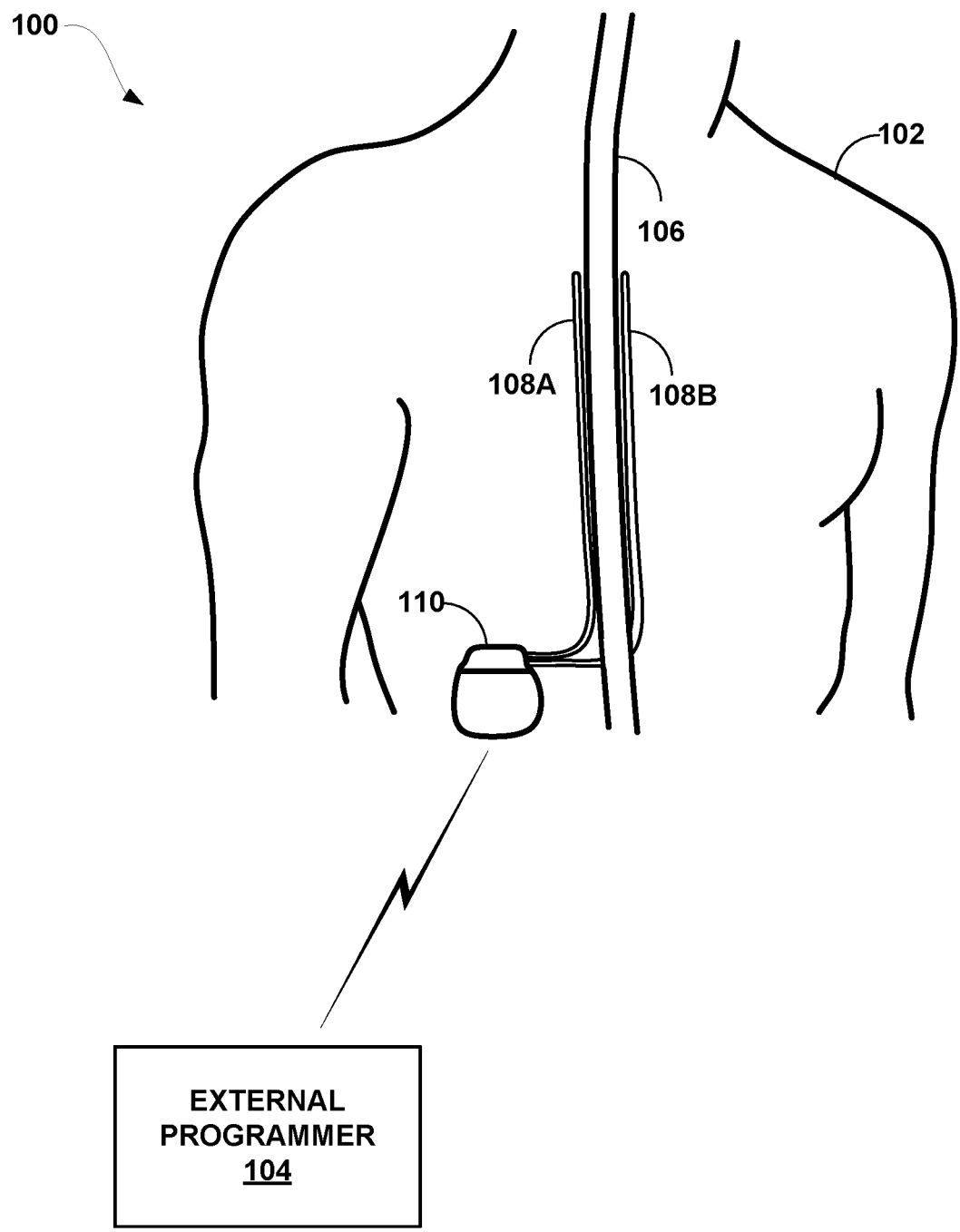
FIG. 1 is a conceptual diagram illustrating an example system that includes a medical device programmer and an IMD according to the techniques of the disclosure.

The disclosure describes examples of medical devices, systems, and techniques for adjusting electrical stimulation delivered to a patient based on a posture state of the patient and one or more characteristics of ECAP signals. Electrical stimulation therapy is typically delivered to a target tissue (e.g., nerves of the spinal cord or muscle) of a patient via two or more electrodes. Parameters of the electrical stimulation therapy (e.g., electrode combination, voltage or current amplitude, pulse width, pulse frequency, etc.) are selected by a clinician and/or the patient to provide relief from various symptoms, such as pain, nervous system disorders, muscle disorders, etc. However, as the patient moves, the distance between the electrodes and the target tissues changes. Since neural recruitment at the nerves is a function of stimulation intensity (e.g., amplitude and/or pulse frequency) and distance between the target tissue and the electrodes, movement of the electrode closer to the target tissue may result in increased neural recruitment (e.g., possible painful sensations or adverse motor function), and movement of the electrode further from the target tissue may result in decreased efficacy of the therapy for the patient. Certain patient postures (which may or may not include patient activity) may be representative of respective distances (or changes in distance) between electrodes and nerves and thus be an informative feedback variable for modulating stimulation therapy.

In some examples, a patient may experience discomfort or pain caused by transient patient conditions, which is referred to herein as transient overstimulation. The electrodes can move closer to the target tissue for a number of reasons including coughing, sneezing, laughing, valsalva maneuvers, leg lifting, cervical motions, deep breathing, or another transient patient movement. If a system is delivering stimulation during these movements, the patient may perceive the stimulation as stronger (and possibly uncomfortable) due to the decreased distance between electrodes and target tissue in a short amount of time. Although a patient may anticipate such movements and preemptively reduce stimulation intensity in an attempt to avoid these uncomfortable sensations, these patient actions interfere with normal activities and may not be sufficient to avoid uncomfortable stimulation at all times.

ECAPs are a measure of neural recruitment because each ECAP signal represents the superposition of electrical potentials generated from a population of axons firing in response to an electrical stimulus (e.g., a stimulation pulse). Changes in a characteristic (e.g., an amplitude of a portion of the signal or area under the curve of the signal) of an ECAP signals occur as a function of how many axons have been activated by the delivered stimulation pulse. For a given set of parameter values that define the stimulation pulse and a given distance between the electrodes and target nerve, the detected ECAP signal may have a certain characteristic value (e.g., amplitude, or area under a curve). Therefore, a system can determine that the distance between electrodes and nerves has increased or decreased in response to determining that the measured ECAP characteristic value has increased or decreased. For example, if the set of parameter values stays the same and the ECAP characteristic value of amplitude increases, the system can determine that the distance between electrodes and the nerve has decreased.

In some examples, effective stimulation therapy may rely on a certain level of neural recruitment at a target nerve. This effective stimulation therapy may provide relief from one or more conditions (e.g., patient perceived pain) without an unacceptable level of side effects (e.g., overwhelming perception of stimulation). However, if the patient changes posture or otherwise engages in physical activity, the distance between the electrodes and the nerve changes as well. This change in distance can cause loss of effective therapy and/or side effects if the parameter values that define stimulation are not adjusted to compensate for the change in distance. Moreover, the different distance between electrodes and the target nerve (e.g., caused by a shift from one posture state to another) may also result in different sensitivities to stimulation intensity (e.g., smaller distances may result in greater sensitivities to changes in stimulation intensity). If a system does not adjust the control policy for these changes, adjustments to stimulation parameter values may not be sufficient to maintain effective therapy or may provide stimulation that is too strong at that posture state. Therefore, it may be beneficial to maintain effective therapy by the system adjusting how stimulation intensity is changed within a given posture state and/or changing target ECAP characteristic values when a posture state of the patient has changed.

As described herein, systems, devices, and techniques provide solutions to one or more of the above-referenced problems by adjusting electrical stimulation therapy delivered to a patient based on a posture state of the patient and one or more characteristics of ECAP signals. As discussed above, when a patient moves, the distance between implanted electrodes and target nerves changes. For example, electrodes implanted along the spinal column move to a position closer to the spinal cord when a subject lies in a supine posture state as compared to a position farther from the spinal cord when the subject assumes a standing posture state. Since posture state affects the distance between the electrodes and target nerve, the system may detect or otherwise obtain the current posture state of the patient and adjust one or more aspects of the control policy employed by the system to modulate stimulation therapy in response to detected ECAP signals. A posture state may refer to a patient posture, an activity level, or a combination of patient posture and activity level. In some examples, the system may select a therapy program or set of stimulation parameter values according to the detected posture state of the patient.

The system may store or otherwise obtain gain values, growth curves, target ECAP characteristic values, or other factors that affect modulation of stimulation associated with respective posture states. Electrical stimulation may be delivered to a patient by the medical device in a train of stimulation pulses, and parameters that define the stimulation pulses may include pulse amplitude (current and/or voltage), pulse frequency, pulse width, pulse shape, and/or electrode combination. The system may alter, adjust, change, or otherwise modulate one or more parameters of the stimulation pulses over time in order to maintain a desired level of stimulation efficacy for the patient.

In one example, the system may monitor one or more characteristic values that represent detected ECAP signals and adjust a stimulation parameter value in an attempt to achieve a target ECAP characteristic value. When adjusting the stimulation parameter value in response to determining that the sensed characteristic value of the ECAP signal is below or above the target ECAP characteristic value, the system may employ a gain value that represents the magnitude, or rate, of change applied to a stimulation parameter in order to achieve the target ECAP characteristic value. The system can then increase or decrease a stimulation parameter according to the gain value in order to maintain the target ECAP characteristic value.

In some examples, the gain value may be a multiplier applied to a difference between a target ECAP characteristic value and a detected ECAP characteristic value. If the gain value is constant, the result is a stimulation parameter value that changes linearly. For example, the system may select one gain value for any detected ECAP characteristic value that is less than the target ECAP characteristic value, and the system may select a different gain value for any detected ECAP characteristic value that is greater than the target ECAP characteristic value. In other examples, the gain value may be calculated using a function that may be linear or non-linear. Put another way, for a given input or set of inputs (e.g., the detected ECAP characteristic value and/or posture state may be an input that affects the calculated gain value) the system may calculate different gain values for increasing stimulation intensity and/or decreasing stimulation intensity.

In one example, the system may determine a gain value that changes for different sensed ECAP characteristic values or different differences between the sensed ECAP characteristic value and a target ECAP characteristic value. A changing gain value (via a linear or non-linear function) would result in a non-linear function that determines the adjusted stimulation parameter (e.g., the output of the non-linear function). For example, the system may adjust the stimulation parameter value exponentially or logarithmically according to the difference between the sensed ECAP characteristic value and the threshold ECAP amplitude. In one example, the gain value is calculated by multiplying the difference between the sensed ECAP characteristic value and the threshold ECAP amplitude to a multiplier (e.g., a linear function) such that the gain value changes according to that difference between the sensed ECAP characteristic value and the threshold ECAP amplitude. In some examples, the gain value may represent a value selected from a table that stores gain values for respective difference values between the sensed ECAP characteristic value and the threshold ECAP amplitude. The table may result in a linear or non-linear function for determining the next stimulation parameter value.

For example, a larger gain value will cause the system to make a larger adjustment to the stimulation parameter for the same stimulation pulse than the adjustment resulting from a smaller gain value. For a non-linear function this comparison in gain value can be made relative to the same value for the difference between the sensed ECAP characteristic value and the threshold ECAP amplitude (e.g., the value difference representing an input value to the gain function). Thus, for a given input value of the gain function (or set of input values) the corresponding gain value (or set of gain values) is changed. For ease of discussion, various examples discuss the change in gain value relative to a linear function. It is understood that a non-linear function may also be used in such embodiments, where the relative change in gain value is thereby relative to the same value for the difference between the sensed ECAP characteristic value and the threshold ECAP amplitude.

Without different gain values for different posture states, a system may respond too slowly or too quickly with adjustments to stimulation parameter values. If the gain value is too large for the posture state, the system may overcorrect a stimulation parameter value (e.g., cause an uncomfortable sensation or reduce therapy efficacy). If the gain value is too small for the posture state, the system may require many iterations of adjustments to the stimulation parameter before the appropriate stimulation intensity is provided (e.g., also causing a prolonged uncomfortable sensation or a prolonged period of ineffective therapy). Generally, posture states associated with farther distances between the electrodes and target nerve may generally have larger gain values than posture states associated with closer distances between the electrodes and target nerve. In this manner, smaller gain values may be associated with smaller distances between electrodes and the target nerve (e.g., posture states more sensitive to changes in stimulation intensity such as a supine posture state). Conversely, larger gain values may be associated with larger distances between electrodes and the target nerve (e.g., posture states less sensitive to changes in stimulation intensity such as a prone posture state). A gain value may be inversely proportional to a growth curve for a particular posture state, wherein the growth curve may be a best fit curve or line of ECAP characteristic values (e.g., voltage amplitude) for given stimulation parameter values (e.g., a current amplitude of the respective pulses that elicited respective ECAP signals). In some examples, the target ECAP characteristic value may be the same for some or all posture states, but the target ECAP characteristic value may be different between posture states in other examples.

In another type of control policy (e.g., type of closed-loop feedback scheme), the system may employ a threshold ECAP characteristic value instead of a target ECAP characteristic value. The system may monitor characteristic values for sensed ECAP signals and reduce one or more stimulation parameter values from a predetermined value only in response to the characteristic value exceeding the threshold ECAP characteristic value. In other words, the system may be configured to attempt to keep characteristic values of sensed ECAP signals below the threshold ECAP characteristic value and only increase the stimulation parameter back up to the predetermined value in response to the characteristic value dropping back below the threshold ECAP characteristic value. In some examples, the system may select the gain value used for adjusting the stimulation parameter according to the current posture state of the patient. In addition, or alternatively, the system may select the threshold ECAP characteristic value according to the detected posture state of the patient.

In some examples, stimulation parameter values may be predetermined and/or automatically adjusted by the system based on characteristic values of ECAP signals, posture states, and other types of feedback. An external programmer for an IMD may provide a variety of features to support association of stimulation parameter values and/or characteristic values of ECAP signals with different posture states. As one example, the programmer may receive user input indicating the posture state that the patient is occupying and associated ECAP signals, and/or corresponding characteristic values, with that posture state. As another example, a patient may indicate a value for a previously undefined stimulation parameter value for a defined posture state while the patient is in the posture state or transitioning to the posture state. The indicated value may be defined for the posture state. As another example, a user may link multiple posture states and select a set of stimulation parameter values for delivery of therapy for each of the linked posture states. In this manner, it may not be necessary to specify separate sets of stimulation parameter values for each individual posture state.

In some examples, a medical device, e.g., an implantable medical device (IMD), that delivers electrical stimulation may also employ a posture state detector (e.g., one or more sensors) that detects the patient posture state. In other examples, the IMD may receive data from one or more a separate devices that sense the posture state of the patient. The IMD may then adjust one or more stimulation parameters in response to different posture states as indicated by the posture state detector.

A user may define stimulation parameter values for delivery of therapy to a patient and associate the stimulation parameter values with multiple posture states based on user input, e.g., simultaneously. As another example, upon storing a set of pre-established posture state definitions for delivery of posture state-responsive therapy, a device may permit a patient to submit a request via a patient programmer to update the set of pre-established posture state definitions. For example, programmer may be configured to receive user input changing the definitions of one or more posture states. In addition, a posture state definition may be modified based on user therapy adjustments and/or posture state information. In some cases, the posture state may be expanded and split. In other cases, the posture state may be reduced in size based on posture state information. Hence, using one or more of the features described in this disclosure, stimulation parameter values may be flexibly, conveniently, and efficiently specified for various posture states, including predetermined posture states and patient-created posture states.

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal than may have a sinusoidal waveform or other continuous waveform.

FIG. 1 is a conceptual diagram illustrating example system 100 that includes implantable medical device (IMD) 110 to deliver electrical stimulation therapy to patient 102. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in FIG. 1, system 100 includes an IMD 110, leads 108A and 108B, and external programmer 104 shown in conjunction with a patient 102, who is ordinarily a human patient. In the example of FIG. 1, IMD 110 is an implantable electrical stimulator that is configured to generate and deliver electrical stimulation therapy to patient 102 via one or more electrodes of electrodes of leads 108A and/or 108B (collectively, "leads 108"), e.g., for relief of chronic pain or other symptoms. In other examples, IMD 110 may be coupled to a single lead carrying multiple electrodes or more than two leads each carrying multiple electrodes. In some examples, the stimulation signals, or pulses, may be configured to elicit detectable ECAP signals that IMD 110 may use to determine the posture state occupied by patient 102 and/or determine how to adjust one or more parameters that define stimulation therapy. IMD 110 may be a chronic electrical stimulator that remains implanted within patient 102 for weeks, months, or even years. In other examples, IMD 110 may be a temporary, or trial, stimulator used to screen or evaluate the efficacy of electrical stimulation for chronic therapy. In one example, IMD 110 is implanted within patient 102, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2) within patient 102. In this example, IMD 110 may be constructed with a biocompatible housing, such as titanium or stainless steel, or a polymeric material such as silicone, polyurethane, or a liquid crystal polymer, and surgically implanted at a site in patient 102 near the pelvis, abdomen, or buttocks. In other examples, IMD 110 may be implanted within other suitable sites within patient 102, which may depend, for example, on the target site within patient 102 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 102 via one or more electrodes (not shown) of implantable leads 108. In the example of FIG. 1, leads 108 carry electrodes that are placed adjacent to the target tissue of spinal cord 106. One or more of the electrodes may be disposed at a distal tip of a lead 108 and/or at other positions at intermediate points along the lead. Leads 108 may be implanted and coupled to IMD 110. The electrodes may transfer electrical stimulation generated by an electrical stimulation generator in IMD 110 to tissue of patient 102. Although leads 108 may each be a single lead, lead 108 may include a lead extension or other segments that may aid in implantation or positioning of lead 108. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 108 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 108 will be described for purposes of illustration.

The deployment of electrodes via leads 108 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 108 are linear leads having 8 ring electrodes along the axial length of the lead. In another example, the electrodes are segmented rings arranged in a linear fashion along the axial length of the lead and at the periphery of the lead.

The stimulation parameter set of a therapy stimulation program that defines the stimulation pulses of electrical stimulation therapy by IMD 110 through the electrodes of leads 108 may include information identifying which electrodes have been selected for delivery of stimulation according to a stimulation program, the polarities of the selected electrodes, i.e., the electrode combination for the program, voltage or current amplitude, pulse frequency, pulse width, pulse shape of stimulation delivered by the electrodes. These stimulation parameters values that make up the stimulation parameter set that defines pulses may be predetermined parameter values defined by a user and/or automatically determined by system 100 based on one or more factors or user input.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 102.

In some examples, lead 108 includes one or more sensors configured to allow IMD 110 to monitor one or more parameters of patient 102, such as patient activity, pressure, temperature, or other characteristics. The one or more sensors may be provided in addition to, or in place of, therapy delivery by lead 108.

IMD 110 is generally configured to deliver electrical stimulation therapy to patient 102 via selected combinations of electrodes carried by one or both of leads 108, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 106, such as within an intrathecal space or epidural space of spinal cord 106, or, in some examples, adjacent nerves that branch off spinal cord 106. Leads 108 may be introduced into spinal cord 106 in via any suitable region, such as the thoracic, cervical or lumbar regions. Stimulation of spinal cord 106 may, for example, prevent pain signals from traveling through spinal cord 106 and to the brain of patient 102. Patient 102 may perceive the interruption of pain signals as a reduction in pain and, therefore, efficacious therapy results. In other examples, stimulation of spinal cord 106 may produce paresthesia which may be reduce the perception of pain by patient 102, and thus, provide efficacious therapy results.

IMD 110 is configured to generate and deliver electrical stimulation therapy to a target stimulation site within patient 102 via the electrodes of leads 108 to patient 102 according to one or more therapy stimulation programs. A therapy stimulation program defines values for one or more parameters (e.g., a parameter set) that define an aspect of the therapy delivered by IMD 110 according to that program. For example, a therapy stimulation program that controls delivery of stimulation by IMD 110 in the form of pulses may define values for voltage or current pulse amplitude, pulse width, pulse rate (e.g., pulse frequency), electrode combination, pulse shape, etc. for stimulation pulses delivered by IMD 110 according to that program.

A user, such as a clinician or patient 102, may interact with a user interface of an external programmer 104 to program IMD 110. Programming of IMD 110 may refer generally to the generation and transfer of commands, programs, or other information to control the operation of IMD 110. In this manner, IMD 110 may receive the transferred commands and programs from external programmer 104 to control stimulation, such as stimulation pulses that provide electrical stimulation therapy. For example, external programmer 104 may transmit therapy stimulation programs, stimulation parameter adjustments, therapy stimulation program selections, posture states, user input, or other information to control the operation of IMD 110, e.g., by wireless telemetry or wired connection.

In some cases, external programmer 104 may be characterized as a physician or clinician programmer if it is primarily intended for use by a physician or clinician. In other cases, external programmer 104 may be characterized as a patient programmer if it is primarily intended for use by a patient. A patient programmer may be generally accessible to patient 102 and, in many cases, may be a portable device that may accompany patient 102 throughout the patient's daily routine. For example, a patient programmer may receive input from patient 102 when the patient wishes to terminate or change electrical stimulation therapy, or when a patient perceives stimulation being delivered. In general, a physician or clinician programmer may support selection and generation of programs by a clinician for use by IMD 110, whereas a patient programmer may support adjustment and selection of such programs by a patient during ordinary use. In other examples, external programmer 104 may include, or be part of, an external charging device that recharges a power source of IMD 110. In this manner, a user may program and charge IMD 110 using one device, or multiple devices.

As described herein, information may be transmitted between external programmer 104 and IMD 110. Therefore, IMD 110 and external programmer 104 may communicate via wireless communication using any techniques known in the art. Examples of communication techniques may include, for example, radiofrequency (RF) telemetry and inductive coupling, but other techniques are also contemplated. In some examples, external programmer 104 includes a communication head that may be placed proximate to the patient's body near the IMD 110 implant site to improve the quality or security of communication between IMD 110 and external programmer 104. Communication between external programmer 104 and IMD 110 may occur during power transmission or separate from power transmission.

In some examples, IMD 110, in response to commands from external programmer 104, delivers electrical stimulation therapy according to a plurality of therapy stimulation programs to a target tissue site of the spinal cord 106 of patient 102 via electrodes (not depicted) on leads 108. In some examples, IMD 110 modifies therapy stimulation programs as therapy needs of patient 102 evolve over time. For example, the modification of the therapy stimulation programs may cause the adjustment of at least one parameter of the plurality of stimulation pulses. When patient 102 receives the same therapy for an extended period, the efficacy of the therapy may be reduced. In some cases, parameters of the plurality of stimulation pulses may be automatically updated.

As described herein, IMD 110 may be configured to detect ECAP signals which are representative of the number of nerve fibers activated by a delivered stimulation signal (e.g., a delivered pulse). Since the distance between electrodes and the target nerve changes for different posture states (e.g., a static posture and/or activity component), a characteristic value of one or more ECAP signals can be indicative of the posture state currently occupied when the one or more ECAP signals were detected by IMD 110. In one example, IMD 110 may deliver a plurality of pulses defined by different parameter values and detect the respective ECAP signal elicited by each pulse. IMD 110 may determine a relationship between characteristic values from each ECAP signal and the different parameter values of the pulses, and this relationship may be different for each different posture state. In one example, the relationship may be a curve of the characteristic values of the ECAP (e.g., an amplitude of the ECAP signal) vs. values of a stimulation parameter (e.g., the current amplitude of the respective pulses) that elicited each ECAP signal from which the characteristic values were derived. Each posture state may have a respective curve that varies in slope and/or intercept. In some examples, a gain value may be determined from the slope of the growth curve, wherein the gain value may be inversely proportional to the slope.

In this disclosure, efficacy of electrical stimulation therapy may be indicated by one or more characteristics (e.g. an amplitude of or between one or more peaks or an area under the curve of one or more peaks) of an action potential that is evoked by a stimulation pulse delivered by IMD 110 (i.e., a characteristic value of the ECAP signal). Electrical stimulation therapy delivery by leads 108 of IMD 110 may cause neurons within the target tissue to evoke a compound action potential that travels up and down the target tissue, eventually arriving at sensing electrodes of IMD 110. Furthermore, stimulation may also elicit at least one ECAP signal, and ECAPs responsive to stimulation may also be a surrogate for the effectiveness of the therapy. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near vertical edge of the pulse, and a low slew rate indicates a longer ramp up (or ramp down) in the amplitude of the pulse. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered stimulation pulses.

Some example techniques for adjusting stimulation parameter values for stimulation pulses (e.g., pulses that may or may not contribute to therapy for the patient) are based on comparing the value of a characteristic of a measured ECAP signal to a target ECAP characteristic value. In response to delivering a stimulation pulse defined by a set of stimulation parameter values, IMD 110, via two or more electrodes interposed on leads 108, senses electrical potentials of tissue of the spinal cord 106 of patient 102 to measure the electrical activity of the tissue. IMD 110 senses ECAPs from the target tissue of patient 102, e.g., with electrodes on one or more leads 108 and associated sense circuitry. In some examples, IMD 110 receives a signal indicative of the ECAP from one or more sensors, e.g., one or more electrodes and circuitry, internal or external to patient 102. Such an example signal may include a signal indicating an ECAP of the tissue of patient 102. Examples of the one or more sensors include one or more sensors configured to measure a compound action potential of patient 102, or a physiological effect indicative of a compound action potential. For example, to measure a physiological effect of a compound action potential, the one or more sensors may be an accelerometer, a pressure sensor, a bending sensor, a sensor configured to detect a posture of patient 102, or a sensor configured to detect a respiratory function of patient 102. However, in other examples, external programmer 104 receives a signal indicating a compound action potential in the target tissue of patient 102 and transmits a notification to IMD 110.

In the example of FIG. 1, IMD 110 is described as performing a plurality of processing and computing functions. However, external programmer 104 instead may perform one, several, or all of these functions. In this alternative example, IMD 110 functions to relay sensed signals to external programmer 104 for analysis, and external programmer 104 transmits instructions to IMD 110 to adjust the one or more parameters defining the electrical stimulation therapy based on analysis of the sensed signals. For example, IMD 110 may relay the sensed signal indicative of an ECAP to external programmer 104. External programmer 104 may compare the parameter value of the ECAP to the target ECAP characteristic value, and in response to the comparison, external programmer 104 may instruct IMD 110 to adjust one or more stimulation parameter that defines the electrical stimulation informed pulses and, in some examples, control pulses, delivered to patient 102.

In some examples, the system changes the target ECAP characteristic value and/or growth rate(s) over a period of time, such as according to a change to a stimulation threshold (e.g., a perception threshold or detection threshold specific for the patient). The system may be programmed to change the target ECAP characteristic in order to adjust the intensity of informed pulses to provide varying sensations to the patient (e.g., increase or decrease the volume of neural activation). Although the system may change the target ECAP characteristic value, received ECAP signals may still be used by the system to adjust one or more parameter values of the informed pulses and/or control pulses in order to meet the target ECAP characteristic value.

One or more devices within system 100, such as IMD 110 and/or external programmer 104, may perform various functions as described herein. For example, IMD 110 may include stimulation circuitry configured to deliver electrical stimulation, sensing circuitry configured to sense a plurality ECAP signals, and processing circuitry. The processing circuitry may be configured to control the stimulation circuitry to deliver a plurality of electrical stimulation pulses having different amplitude values and control the sensing circuitry to detect, after delivery of each electrical stimulation pulse of the plurality of electrical stimulation pulses, a respective ECAP signal of the plurality of ECAP signals. The processing circuitry of IMD 110 may then determine, based on the plurality of ECAP signals, a posture state of the patient.

As described herein, IMD 110 may modulate or adjust one or more stimulation parameters that at least partially define electrical stimulation based on a detected posture state of the patient 102. IMD 110 may use the detected posture state to determine how to employ ECAP signals in a closed-loop feedback system for adjusting stimulation parameters. In one example, IMD 110 includes stimulation generation circuitry configured to generate and deliver electrical stimulation to patient 102 according one or more sets of stimulation parameters that at least partially define the pulses of the electrical stimulation. Each set of stimulation parameters may include at least one of an amplitude, a pulse width, a pulse frequency, or a pulse shape.

IMD 110 may also include sensing circuitry configured to sense an ECAP signal elicited by delivered electrical stimulation, such as a stimulation pulse. IMD 110 may also include processing circuitry configured to control delivery of the electrical stimulation to patient 102 according to a first value of a stimulation parameter and determine a characteristic value of the ECAP signal detected from the electrical stimulation. IMD 110 may also receive, from a sensor, a posture state signal representing a posture state of the patient. IMD 110 may then determine, based on the posture state signal, a gain value for the stimulation parameter and adjust, based on the characteristic value of the ECAP signal and the gain value, the first value of the stimulation parameter to a second value of the stimulation parameter. IMD 110 may then control subsequent delivery of the electrical stimulation according to the second value of the stimulation parameter.

In some examples, the processing circuitry of IMD 110 may be configured to adjust the first value to the second value by one of increasing or decreasing the stimulation parameter of the electrical stimulation based on a growth curve associated with the posture state of the patient. As discussed herein, the growth curve may represent a relationship between one or more parameters of delivered stimulation pulses and a characteristic of ECAP signals. For example, the characteristic may be an amplitude of the ECAP signals (e.g., an amplitude between an N1 peak and a P2 peak of the ECAP signal), an area under one or more peaks of the ECAP signal, or some other metric indicative of the nerve activation that resulted in the ECAP signal. In some examples, the gain value may be inversely proportional to a slope of the growth curve.

When IMD 110 is configured to modulate stimulation pulses in order to maintain consistent nerve activation, such as increasing and decreasing a stimulation parameter to maintain a target ECAP characteristic value, IMD 110 may perform an example process. For example, IMD 110 may monitor an amplitude that is the characteristic value of the detected ECAP signal. IMD 110 may adjust the first value to the second value of the stimulation parameter by subtracting the amplitude from a target ECAP amplitude value for the patient to generate a differential amplitude. The differential amplitude is the difference between the detected amplitude and the target ECAP amplitude value. IMD 110 may then multiply the differential amplitude by the gain value that at least partially defines the electrical stimulation to generate a differential value. The gain value may be a multiplier or fraction selected based on the detected posture state. A larger gain value may be associated with posture states at which the distance between electrodes and the target nerve is larger because the distance causes less sensitivity for changes in stimulation pulse intensity. IMD 110 may then add the differential value to a previous amplitude value (e.g., the amplitude value of the last stimulation pulse that was delivered or elicited the ECAP signal) to generate the second value that at least partially defines the next stimulation pulses to be delivered to patient 102.

In other examples, IMD 110 may not attempt to maintain consistent nerve activation by modulating stimulation pulses to achieve a target ECAP characteristic value. Instead, IMD 110 may monitor characteristic values of ECAP signals any only take action when the characteristic value exceeds a threshold ECAP characteristic value. Characteristic values exceeding the threshold ECAP characteristic values may be indicative of increased stimulation perception that may be above an uncomfortable threshold or pain threshold for the patient. Therefore, reducing stimulation pulse intensity when the characteristic value exceeds this level of stimulation may reduce the likelihood that patient 102 experiences any uncomfortable sensations that may occur as a result of posture state changes or any transient movement. For example, IMD 110 may be configured to compare the characteristic value of the ECAP signal to a threshold ECAP characteristic value and determine that the characteristic value of the ECAP signal is greater than the threshold ECAP characteristic value. Responsive to determining that the characteristic value of the ECAP signal is greater than the threshold ECAP characteristic value, IMD 110 may be configured to decrease the first value to the second value for the stimulation parameter of a subsequent stimulation pulse.

IMD 110 may continue to decrease the stimulation parameter value as long as the ECAP characteristic value continues to exceed the threshold ECAP characteristic value. Once, the stimulation parameter has been decreased, IMD 110 may attempt to increase the stimulation parameter value again back up to the predetermined first value intended for the stimulation pulses. IMD 110 may be configured to determine a other characteristic values of subsequent ECAP signals elicited from electrical stimulation pulses delivered after sensing the first ECAP signal. In response to determining that another characteristic value of the subsequent ECAP signals decreases below the threshold ECAP characteristic value, IMD 110 may then increase the value of the stimulation parameter back up to a value limited to be less than or equal to the first value (e.g., back up to the predetermined value for stimulation pulses that may be determined by a set of stimulation parameters or therapy program). In some examples, IMD 110 may iteratively increase the stimulation parameter value until the first value, or original value, is again reached after the characteristic values of the ECAP signal remain below the threshold ECAP characteristic value. IMD 110 may increase the stimulation parameter values at a slower rate than the stimulation parameter values are decreased, but, in other examples, IMD 110 may increase and decrease the stimulation parameters at the same rates.

The detected posture state may be one posture state of a plurality of posture states. In some examples, each posture state may be associated with a respective growth curve representing the relationship between the ECAP values and stimulation parameter values when the patient occupies that particular posture state. In some examples, IMD 110 may select, based on the posture state signal, the gain value from a plurality of gain values associated with respective posture states. The gain value may represent at least one of an increment rate (e.g., how fast IMD 110 should increase the stimulation parameter value) or a decrement rate (e.g., how slow IMD 110 should decrease the stimulation parameter value) for the stimulation parameter that at least partially defines electrical stimulation pulses. In other examples, the gain value may represent a particular magnitude that IMD 110 should increment or decrement a previous parameter value each time IMD 110 increases or decrease the parameter value. This particular magnitude may effectively result in a rate of change at which IMD 110 can adjust a stimulation parameter value. In addition, or alternatively, IMD 110 may select the target ECAP characteristic value or the threshold ECAP characteristic value according to the detected posture state. A patient may or may not benefit from posture state specific target or threshold ECAP characteristic values.

IMD 110 may sense the posture state of patient 102 at predetermined intervals or during predetermined periods of time. In some examples, IMD 110 may sense the posture state in response to a trigger event, such as a patient-requested change in stimulation therapy, a sensed event representative of a patient condition such as pain, or any other triggers. In some examples, IMD 110 may modulate posture state sensing frequency based on whether or not posture state changes are detected. For example, IMD 110 may determine, from at least the signal representing the posture state of the patient, that the posture state of the patient has changed. Responsive to determining that the posture state has changed, IMD 110 may change at least one of an ECAP sensing frequency. IMD 110 may increase posture state sensing frequency when more posture state changes are expected and decrease posture state sensing frequency when fewer posture state changes are expected. Sensing frequency may refer to sensor sampling frequency and/or frequency at which processing circuitry analyzes data obtained from one or more sensors. In this manner, IMD 110 may modulate sensing frequency to conserve power consumption or otherwise reduce processing tasks.

As discussed herein, some example techniques for adjusting stimulation parameter values for electrical stimulation signals are based on comparing the value of a characteristic of a measured ECAP signal to a target ECAP characteristic value or using stimulation parameter values at a determined target ECAP characteristic to inform adjustment of one or more parameter values to maintain the target ECAP according to known relationships between parameters. For example, during delivery of an electrical stimulation signal, IMD 110, via two or more electrodes interposed on leads 108, senses electrical potentials of tissue of the spinal cord 106 of patient 102 to measure the electrical activity of the tissue. IMD 110 senses ECAPs from the target tissue of patient 102, e.g., with electrodes on one or more leads 108 and associated sensing circuitry. In some examples, IMD 110 receives a signal indicative of the ECAP from one or more sensors, e.g., one or more electrodes and circuitry, internal or external to patient 102. Such an example signal may include a signal indicating an ECAP of the tissue of the patient 102. Examples of the one or more sensors include one or more sensors can measure a compound action potential of the patient 102, or a physiological effect indicative of a compound action potential. For example, to measure a physiological effect of a compound action potential, the one or more sensors may be an accelerometer, a pressure sensor, a bending sensor, a sensor can detect a posture of patient 102, or a sensor can detect a respiratory function of patient 102. However, in other examples, external programmer 104 receives a signal indicating a compound action potential in the target tissue of patient 102 and transmits a notification to IMD 110.

In the example of FIG. 1, IMD 110 described as performing a plurality of processing and computing functions. However, external programmer 104 instead may perform one, several, or all of these functions. In this alternative example, IMD 110 functions to relay sensed signals to external programmer 104 for analysis, and external programmer 104 transmits instructions to IMD 110 to adjust the one or more parameters defining the electrical stimulation signal based on analysis of the sensed signals. For example, IMD 110 may relay the sensed signal indicative of an ECAP to external programmer 104. External programmer 104 may compare the parameter value of the ECAP to the target ECAP characteristic value, and in response to the comparison, external programmer 104 may instruct IMD 110 to adjust one or more parameters that define the electrical stimulation signal.

In the example techniques described herein, the stimulation parameter values, growth curves, posture states, and the target ECAP characteristic values (e.g., values of the ECAP indicative of target stimulation intensity) may be initially set at the clinic but may be set and/or adjusted at home by patient 102. Once the target ECAP characteristic values are set, the example techniques allow for automatic adjustment of stimulation parameters to maintain consistent volume of neural activation and consistent perception of therapy for the patient when the electrode-to-neuron distance changes. The ability to change the stimulation parameter values may also allow the therapy to have long term efficacy, with the ability to keep the intensity of the stimulation (e.g., as indicated by the ECAP) consistent by comparing the measured ECAP values to the target ECAP characteristic value. IMD 110 may perform these changes without intervention by a physician or patient 102.

In some examples, the system may change the target ECAP characteristic value over a period of time (e.g., based on a sensed posture state or change in patient conditions). The system may be programmed to change the target ECAP characteristic in order to adjust the intensity of the electrical stimulation signal to provide varying sensations to the patient (e.g., increase or decrease the volume of neural activation). In one example, a system may be programmed to oscillate a target ECAP characteristic value between a maximum target ECAP characteristic value and a minimum target ECAP characteristic value at a predetermined frequency to provide a sensation to the patient that may be perceived as a wave or other sensation that may provide therapeutic relief for the patient. The maximum target ECAP characteristic value, the minimum target ECAP characteristic value, and the predetermined frequency may be stored in the memory of IMD 110 and may be updated in response to a signal from external programmer 104 (e.g., a user request to change the values stored in the memory of IMD 110). In other examples, the target ECAP characteristic value may be programed to steadily increase or steadily decrease to a baseline target ECAP characteristic value over a period of time. In other examples, external programmer 104 may program the target ECAP characteristic value to automatically change over time according to other predetermined functions or patterns. In other words, the target ECAP characteristic value may be programmed to change incrementally by a predetermined amount or predetermined percentage, the predetermined amount or percentage being selected according to a predetermined function (e.g., sinusoid function, ramp function, exponential function, logarithmic function, or the like). Increments in which the target ECAP characteristic value is changed may be changed for every certain number of pulses or a certain unit of time. Although the system may change the target ECAP characteristic value, received ECAP signals may still be used by the system to adjust one or more parameter values of the electrical stimulation signal in order to meet the target ECAP characteristic value.

In some examples, IMD 110 may not be able to measure ECAPs from stimulation that has certain pulse widths and/or pulse frequencies. For example, longer pulse widths and higher pulse frequencies may result in a delivered stimulation pulse overlapping with an ECAP. Since the ECAP amplitude can be much lower amplitude than the stimulation pulse, the stimulation pulse can cover up any ECAP characteristic value of the signal. However, IMD 110 may use measured ECAPs at short pulse widths and/or lower pulse frequencies to identify a combination of stimulation parameter values that produce an ECAP characteristic value (e.g., intensity) that is representative of effective therapy. IMD 110 may then select longer pulse widths and/or higher pulse frequencies according to the relationship between the pulse width and pulse frequency that are estimated to produce a similar ECAP characteristic value that resulted in the effective therapy.

Although in one example IMD 110 takes the form of an SCS device, in other examples, IMD 110 takes the form of any combination of deep brain stimulation (DBS) devices, implantable cardioverter defibrillators (ICDs), pacemakers, cardiac resynchronization therapy devices (CRT-Ds), left ventricular assist devices (LVADs), implantable sensors, orthopedic devices, or drug pumps, as examples.

Figure 2:
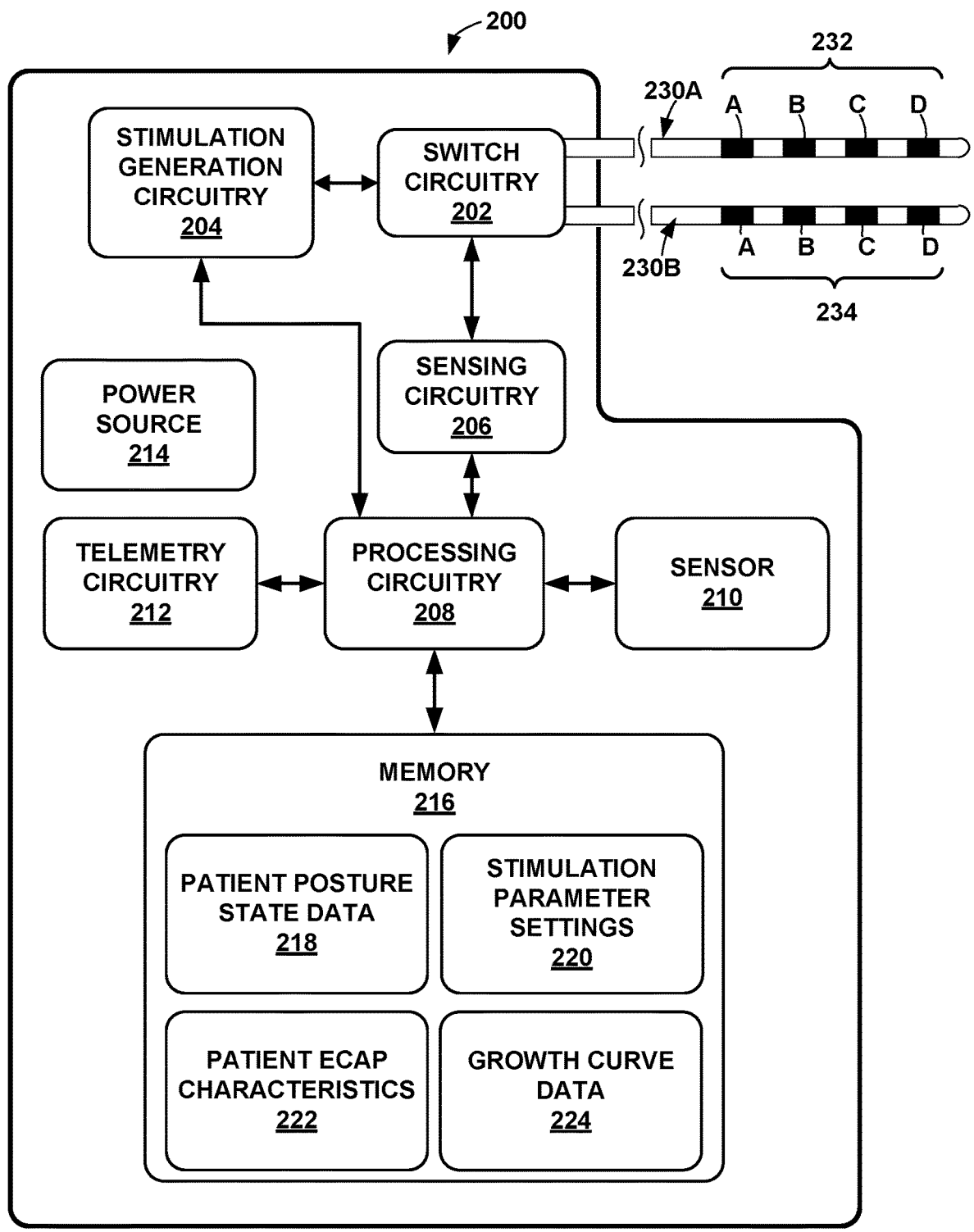
FIG. 2 is a block diagram of the example IMD of FIG. 1.

FIG. 2 is a block diagram of IMD 200. IMD 200 may be an example of IMD 110 of FIG. 1. In the example shown in FIG. 2, IMD 200 includes switch circuitry 202, stimulation generation circuitry 204, sensing circuitry 206, processing circuitry 208, sensor 210, telemetry circuitry 212, power source 214, and memory 216. Each of these circuits may be or include programmable or fixed function circuitry can perform the functions attributed to respective circuitry. For example, processing circuitry 208 may include fixed-function or programmable circuitry, stimulation generation circuitry 204 may include circuitry can generate electrical stimulation signals such as pulses or continuous waveforms on one or more channels, sensing circuitry 206 may include sensing circuitry for sensing signals, and telemetry circuitry 212 may include telemetry circuitry for transmission and reception of signals. Memory 216 may store computer-readable instructions that, when executed by processing circuitry 208, cause IMD 200 to perform various functions described herein. Memory 216 may be a storage device or other non-transitory medium.

In the example shown in FIG. 2, memory 216 stores patient posture state data 218, which may include one or more patient postures, an activity level, or a combination of patient posture and activity level. A set of pre-established posture state definitions for a patient may be stored in patient posture state data 218. A posture state definition may be modified based on user therapy adjustments and/or posture state information. In some cases, the posture state may be expanded and split, or instead, may be reduced in size based on posture state information. The posture state definitions can be automatically updated or updated by a patient, including creating new posture states. Posture states may include, for example, a supine posture, a prone posture, a lying left and/or lying right, a sitting posture, a reclining posture, a standing posture, and/or activities such as running or riding in an automobile.

Memory 216 may store stimulation parameter settings 220 within memory 216 or separate areas within memory 216. Each stored stimulation parameter setting 220 defines values for a set of electrical stimulation parameters (e.g., a stimulation parameter set or therapy program), such as pulse amplitude, pulse width, pulse frequency, electrode combination, pulse burst rate, pulse burst duration, and/or waveform shape. Stimulation parameter settings 220 may also include additional information such as instructions regarding delivery of electrical stimulation signals based on stimulation parameter relationship data, which can include relationships between two or more stimulation parameters based upon data from electrical stimulation signals delivered to patient 102 or data transmitted from external programmer 104. The stimulation parameter relationship data may include measurable aspects associated with stimulation, such as an ECAP characteristic value.

Memory 216 also stores patient ECAP characteristics 222 which may include target ECAP characteristics and/or threshold ECAP characteristic values determined for the patient and/or a history of measured ECAP characteristic values for the patient. Memory 216 may also store growth curve data 224 in separate areas from or as part of patient stimulation parameter settings. Instead of, or in addition to growth curve data 224, memory 216 may include gain values that processing circuitry 208 may use to modulate stimulation pulses as described herein. In other examples, growth curve data 224 may include information regarding relationships between ECAP characteristics and stimulation parameters for one or more posture states.

Accordingly, in some examples, stimulation generation circuitry 204 generates electrical stimulation signals (e.g., pulses) in accordance with the electrical stimulation parameters noted above. Other ranges of stimulation parameter values may also be useful and may depend on the target stimulation site within patient 102. While stimulation pulses are described, stimulation signals may be of any form, such as continuous-time signals (e.g., sine waves) or the like. Switch circuitry 202 may include one or more switch arrays, one or more multiplexers, one or more switches (e.g., a switch matrix or other collection of switches), or other electrical circuitry configured to direct stimulation signals from stimulation generation circuitry 204 to one or more of electrodes 232, 234, or directed sensed signals from one or more of electrodes 232, 234 to sensing circuitry 206. In other examples, stimulation generation circuitry 204 and/or sensing circuitry 206 may include sensing circuitry to direct signals to and/or from one or more of electrodes 232, 234, which may or may not also include switch circuitry 202.

Sensing circuitry 206 may be configured to monitor signals from any combination of electrodes 232, 234. In some examples, sensing circuitry 206 includes one or more amplifiers, filters, and analog-to-digital converters. Sensing circuitry 206 may be used to sense physiological signals, such as ECAPs. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 102. Sensing circuitry 206 may provide signals to an analog-to-digital converter, for conversion into a digital signal for processing, analysis, storage, or output by processing circuitry 208.

Processing circuitry 208 may include any one or more of a microprocessor, a controller, a digital signal processor (DSP), an application specific integrated circuit (ASIC), a field-programmable gate array (FPGA), discrete logic circuitry, or any other processing circuitry can provide the functions attributed to processing circuitry 208 herein may be embodied as firmware, hardware, software or any combination thereof. Processing circuitry 208 controls stimulation generation circuitry 204 to generate electrical stimulation signals according to stimulation parameter settings 220 stored in memory 216 to apply stimulation parameter values, such as pulse amplitude, pulse width, pulse frequency, and waveform shape of each of the electrical stimulation signals.

In the example shown in FIG. 2, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 208 also controls stimulation generation circuitry 204 to generate and apply the electrical stimulation signals to selected combinations of electrodes 232, 234. In some examples, stimulation generation circuitry 204 includes a switch circuit (instead of, or in addition to, switch circuitry 202) that may couple stimulation signals to selected conductors within leads 230, which, in turn, deliver the stimulation signals across selected electrodes 232, 234. Such a switch circuit may be a switch array, switch matrix, multiplexer, or any other type of switch circuitry can selectively couple stimulation energy to selected electrodes 232, 234 and to selectively sense bioelectrical neural signals of a spinal cord of the patient (not shown in FIG. 2) with selected electrodes 232, 234.

In other examples, however, stimulation generation circuitry 204 does not include a switch circuit and switch circuitry 202 does not interface between stimulation generation circuitry 204 and electrodes 232, 234. In these examples, stimulation generation circuitry 204 comprises a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 204, e.g., via switch circuitry 202 and/or switch circuitry of the stimulation generation circuitry 204, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 204 and processing circuitry 208 in FIG. 2, in other examples, sensing circuitry 206 may be in a separate housing from IMD 200 and may communicate with processing circuitry 208 via wired or wireless communication techniques.

In some examples, one or more of electrodes 232 and 234 may be suitable for sensing ECAPs. For instance, electrodes 232 and 234 may sense the voltage amplitude of a portion of the ECAP signals, where the sensed voltage amplitude is a characteristic the ECAP signal.

Memory 216 may be configured to store information within IMD 200 during operation. Memory 216 may include a computer-readable storage medium or computer-readable storage device. In some examples, memory 216 includes one or more of a short-term memory or a long-term memory. Memory 216 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, memory 216 is used to store data indicative of instructions for execution by processing circuitry 208. As discussed herein, memory 216 can store patient posture state data 218, stimulation parameter settings 220, patient ECAP characteristics 222, and growth curve data 224.

Sensor 210 may include one or more sensing elements that sense values of a respective patient parameter. As described, electrodes 232 and 234 may be the electrodes that sense, via sensing circuitry 206, a value of the ECAP indicative of a target stimulation intensity at least partially caused by a set of stimulation parameter values. Sensor 210 may include one or more accelerometers, optical sensors, chemical sensors, temperature sensors, pressure sensors, or any other types of sensors. Sensor 210 may output patient parameter values that may be used as feedback to control delivery of electrical stimulation signals. IMD 200 may include additional sensors within the housing of IMD 200 and/or coupled via one of leads 108 or other leads. In addition, IMD 200 may receive sensor signals wirelessly from remote sensors via telemetry circuitry 212, for example. In some examples, one or more of these remote sensors may be external to patient (e.g., carried on the external surface of the skin, attached to clothing, or otherwise positioned external to the patient). In some examples, signals from sensor 210 may indicate a posture state (e.g., sleeping, awake, sitting, standing, or the like), and processing circuitry 208 may select target and/or threshold ECAP characteristic values according to the indicated posture state. In this manner, processing circuitry 208 may be configured to determine the currently occupied posture state of patient 102.

Telemetry circuitry 212 supports wireless communication between IMD 200 and an external programmer (not shown in FIG. 2) or another computing device under the control of processing circuitry 208. Processing circuitry 208 of IMD 200 may receive, as updates to programs, values for various stimulation parameters such as amplitude and electrode combination, from the external programmer via telemetry circuitry 212. Updates to stimulation parameter settings 220 and input efficacy threshold settings 226 may be stored within memory 216. Telemetry circuitry 212 in IMD 200, as well as telemetry circuits in other devices and systems described herein, such as the external programmer, may accomplish communication by radiofrequency (RF) communication techniques. In addition, telemetry circuitry 212 may communicate with an external medical device programmer (not shown in FIG. 2) via proximal inductive interaction of IMD 200 with the external programmer. The external programmer may be one example of external programmer 104 of FIG. 1. Accordingly, telemetry circuitry 212 may send information to the external programmer on a continuous basis, at periodic intervals, or upon request from IMD 110 or the external programmer.

Power source 214 delivers operating power to various components of IMD 200. Power source 214 may include a rechargeable or non-rechargeable battery and a power generation circuit to produce the operating power. Recharging may be accomplished through proximal inductive interaction between an external charger and an inductive charging coil within IMD 200. In other examples, traditional primary cell batteries may be used. In some examples, processing circuitry 208 may monitor the remaining charge (e.g., voltage) of power source 214 and select stimulation parameter values that may deliver similarly effective therapy at lower power consumption levels when needed to extend the operating time of power source 214. For example, power source 214 may switch to a lower pulse frequency based on the relationships of parameters that may provide similar ECAP characteristic values.

According to the techniques of the disclosure, stimulation generation circuitry 204 of IMD 200 receives, via telemetry circuitry 212, instructions to deliver electrical stimulation according to stimulation parameter settings 220 to a target tissue site of the spinal cord of the patient via a plurality of electrode combinations of electrodes 232, 234 of leads 230 and/or a housing of IMD 200. Each electrical stimulation signal may elicit an ECAP that is sensed by sensing circuitry 206 via electrodes 232 and 234. Processing circuitry 208 may receive, via an electrical signal sensed by sensing circuitry 206, information indicative of an ECAP signal (e.g., a numerical value indicating a characteristic of the ECAP in electrical units such as voltage or power) produced in response to the electrical stimulation signal(s). Stimulation parameter settings 220 may be updated according to the ECAPs recorded at sensing circuitry 206 according to the following techniques.

In one example, the plurality of pulses each have a pulse width of greater than approximately 300 us and less than approximately 2000 μs (i.e., 2 milliseconds). In some examples, the pulse width is greater than approximately 300 μs and less than approximately 900 μs. In another example, the pulse width is greater than approximately 300 μs and less than approximately 500 μs. In one example, the pulses have a pulse width of approximately 450 us and a pulse frequency of approximately 60 Hertz. Amplitude (current and/or voltage) for the pulses may be between approximately 0.5 mA (or volts) and approximately 10 mA (or volts), although amplitude may be lower or greater in other examples.

In one example, the predetermined pulse frequency of the plurality of pulses may be less than approximately 400 Hertz. In some examples, the predetermined pulse frequency of the plurality of pulses may be between approximately 50 Hertz and 70 Hertz. In one example, the predetermined pulse frequency of the plurality of pulses may be approximately 60 Hertz. However, the pulses may have frequencies greater than 400 Hertz or less than 50 Hertz in other examples. In addition, the pulses may be delivered in bursts of pulses, with interburst frequencies of the pulses being low enough such that a sensed ECAP can still fit within the window between consecutive pulses delivered within the burst of pulses. In any example, processing circuitry 208 may be configured to detect ECAPs elicited from respective stimulation pulses.

Processing circuitry 208 may be configured to compare one or more characteristics of ECAPs sensed by sensing circuitry 206 with target ECAP characteristics stored in memory 216 (e.g., patient ECAP characteristics 222). For example, processing circuitry 208 can determine the amplitude of each ECAP signal received at sensing circuitry 206, and processing circuitry 208 can determine the representative amplitude of at least one respective ECAP signal and compare the representative amplitude of a series of ECAP signals to a target ECAP.

In other examples, processing circuitry 208 may use the representative amplitude of the at least one respective ECAP to change other parameters of stimulation pulses to be delivered, such as pulse width, pulse frequency, and pulse shape. All of these parameters may contribute to the intensity of the stimulation pulses, and changing one or more of these parameter values may effectively adjust the stimulation pulse intensity to compensate for the changed distance between the stimulation electrodes and the nerves indicated by the characteristic (e.g., a representative amplitude) of the ECAP signals.

In some examples, leads 230 may be linear 8-electrode leads (not pictured); sensing and stimulation delivery may each be performed using a different set of electrodes. In a linear 8-electrode lead, each electrode may be numbered consecutively from 0 through 7. For instance, a pulse may be generated using electrode 1 as a cathode and electrodes 0 and 2 as anodes (e.g., a guarded cathode), and a respective ECAP signal may be sensed using electrodes 6 and 7, which are located on the opposite end of the electrode array. This strategy may minimize the interference of the stimulation pulse with the sensing of the respective ECAP. Other electrode combinations may be implemented, and the electrode combinations may be changed using the patient programmer via telemetry circuitry 212. For example, stimulation electrodes and sensing electrodes may be positioned closer together. Shorter pulse widths for the nontherapeutic pulses may allow the sensing electrodes to be closer to the stimulation electrodes.

In one example, sensor 210 may detect a change in posture state, including activity or a change in posture of the patient. Processing circuitry 208 may receive an indication from sensor 210 that the activity level or posture of the patient is changed, and processing circuitry 208 can initiate or change the delivery of the plurality of pulses according to stimulation parameter settings 220. For example, processing circuitry 208 may increase the frequency of pulse delivery and respective ECAP sensing in response to receiving an indication that the patient activity has increased, which may indicate that the distance between electrodes and nerves will likely change. Alternatively, processing circuitry 208 may decrease the frequency of pulse delivery and respective ECAP sensing in response to receiving an indication that the patient activity has decreased. In some examples, one or more therapy parameters (e.g., frequency, amplitude, slew rate, pulse width, or the like) may be adjusted (e.g., increased or decreased) in response to receiving an indication that the patient posture state has changed. Processing circuitry 208 can update patient posture state data 218 and growth curve data 224 according to the signal received from sensor 210.

Figure 3:
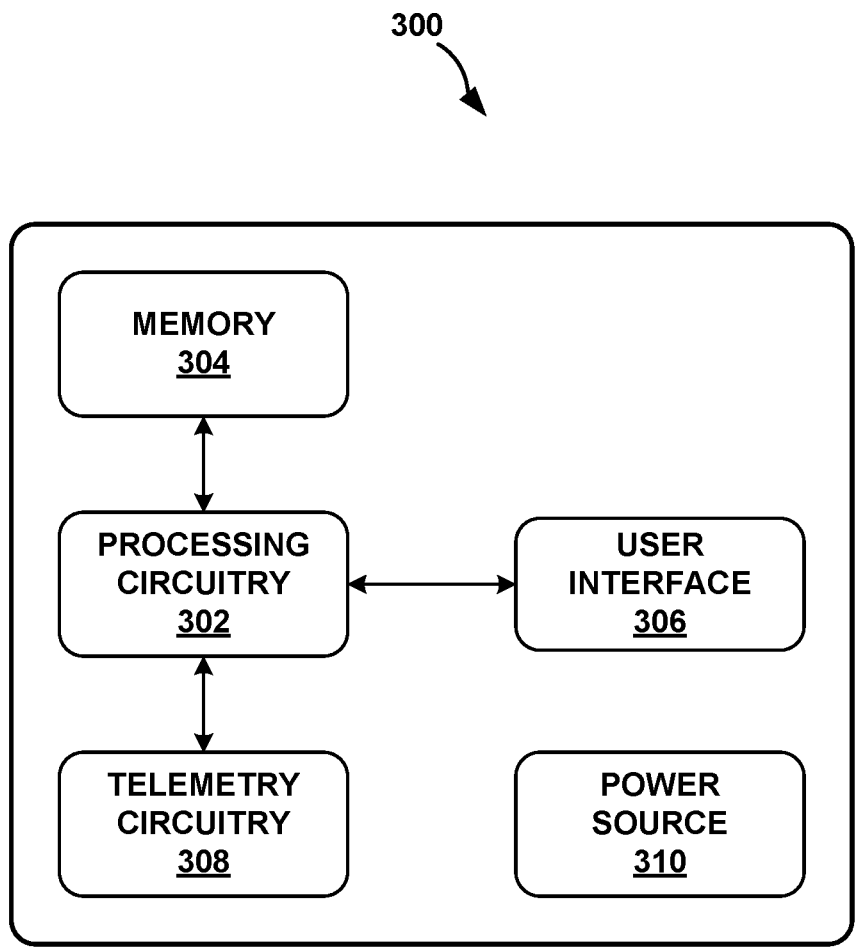
FIG. 3 is a block diagram of the example external programmer of FIG. 1.

FIG. 3 is a block diagram of the example external programmer 300. External programmer 300 may be an example of external programmer 104 of FIG. 1. Although programmer 300 may generally be described as a hand-held device, external programmer 300 may be a larger portable device or a more stationary device. In addition, in some examples, external programmer 300 may be included as part of an external charging device or include the functionality of an external charging device. As illustrated in FIG. 3, external programmer 300 may include a processing circuitry 302, memory 304, user interface 306, telemetry circuitry 308, and power source 310. Storage device 304 may store instructions that, when executed by processing circuitry 302, cause processing circuitry 302 and external programmer 300 to provide the functionality ascribed to external programmer 300 throughout this disclosure. Each of these components, circuitry, or modules, may include electrical circuitry that can perform some, or all of the functionality described herein. For example, processing circuitry 302 may include processing circuitry to perform the processes discussed with respect to processing circuitry 302.

In general, programmer 300 comprises any suitable arrangement of hardware, alone or in combination with software and/or firmware, to perform the techniques attributed to programmer 300, and processing circuitry 302, user interface 306, and telemetry circuitry 308 of programmer 300. In various examples, programmer 300 may include one or more processors, such as one or more microprocessors, DSPs, ASICs, FPGAs, or any other equivalent integrated or discrete logic circuitry, as well as any combinations of such components. Programmer 300 also, in various examples, may include a memory 304, such as RAM, ROM, PROM, EPROM, EEPROM, flash memory, a hard disk, a CD-ROM, comprising executable instructions for causing the one or more processors to perform the actions attributed to them. Moreover, although processing circuitry 302 and telemetry circuitry 308 are described as separate, in some examples, processing circuitry 302 and telemetry circuitry 308 are functionally integrated. In some examples, processing circuitry 302 and telemetry circuitry 308 correspond to individual hardware units, such as ASICs, DSPs, FPGAs, or other hardware units.

Memory 304 (e.g., a storage device) may store instructions that, when executed by processing circuitry 302, cause processing circuitry 302 and programmer 300 to provide the functionality ascribed to programmer 300 throughout this disclosure. For example, memory 304 may include instructions that cause processing circuitry 302 to obtain a stimulation parameter setting from memory, select a spatial electrode movement pattern, or receive a user input and send a corresponding command to programmer 300, or instructions for any other functionality. In addition, memory 304 may include a plurality of stimulation parameter settings, where each setting includes a parameter set that defines electrical stimulation. Memory 304 may also store data received from a medical device (e.g., IMD 110). For example, memory 304 may store ECAP related data recorded at a sensing circuitry of the medical device, and memory 304 may also store data from one or more sensors of the medical device.

User interface 306 may include a button or keypad, lights, a speaker for voice commands, a display, such as a liquid crystal (LCD), light-emitting diode (LED), or organic light-emitting diode (OLED). In some examples the display may be a touch screen. User interface 306 can display any information related to the delivery of electrical stimulation, identified patient behaviors, sensed patient parameter values, patient behavior criteria, or any other such information. External programmer 300 may receive user input (e.g., indication of when the patient changes posture states) via user interface 306. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation. In other examples, user interface 306 may receive input from the patient and/or clinician regarding efficacy of the therapy, such as binary feedback, numerical ratings, textual input, etc. In some examples, processing circuitry 302 may interpret patient requests to change therapy as negative feedback regarding the current parameter values used to define therapy.

Telemetry circuitry 308 may support wireless communication between the medical device and programmer 300 under the control of processing circuitry 302. Telemetry circuitry 308 can communicate with another computing device via wireless communication techniques, or direct communication through a wired connection. In some examples, telemetry circuitry 308 provides wireless communication via an RF or proximal inductive medium. In some examples, telemetry circuitry 308 includes an antenna, which may take on a variety of forms, such as an internal or external antenna.

Examples of local wireless communication techniques that may be employed to facilitate communication between programmer 300 and IMD 110 include RF communication according to the 902.11 or Bluetooth specification sets or other standard or proprietary telemetry protocols. In this manner, other external devices may be capable of communicating with programmer 300 without needing to establish a secure wireless connection. As described herein, telemetry circuitry 308 can transmit a spatial electrode movement pattern or other stimulation parameter values to IMD 110 for delivery of electrical stimulation.

In some examples, selection of stimulation parameter settings may be transmitted to the medical device for delivery to the patient. In other examples, stimulation parameter settings may include medication, activities, or other instructions that the patient must perform themselves or a caregiver perform for patient 102. In some examples, external programmer 300 may provide visual, audible, and/or tactile notifications that indicate there are new instructions. External programmer 300 may require receiving user input acknowledging that the instructions have been completed in some examples.

According to the techniques of the disclosure, user interface 306 of external programmer 300 receives an indication from a clinician instructing a processor of the medical device to update one or more patient posture state settings, gain values, growth curve settings, or stimulation parameter settings. Updating the posture state settings, gain values, growth curve settings may cause the stimulation parameter settings to update as well, including changing one or more parameter values of the electrical stimulation signal delivered by the medical device according to the settings, such as pulse amplitude, pulse width, pulse frequency, electrode combination, and/or waveform shape. Gain values and/or growth curve settings may be based upon sensed ECAP signals, posture state data, and stimulation parameter data, in some examples. User interface 306 may also receive instructions from the clinician commanding any electrical stimulation.

Power source 310 can deliver operating power to various components of programmer 300. Power source 310 may be the same as or substantially similar to power source 214. Power source 310 may include a battery and a power generation circuit to produce the operating power. In some examples, the battery is rechargeable to allow extended operation. Recharging may be accomplished by electrically coupling power source 310 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4:
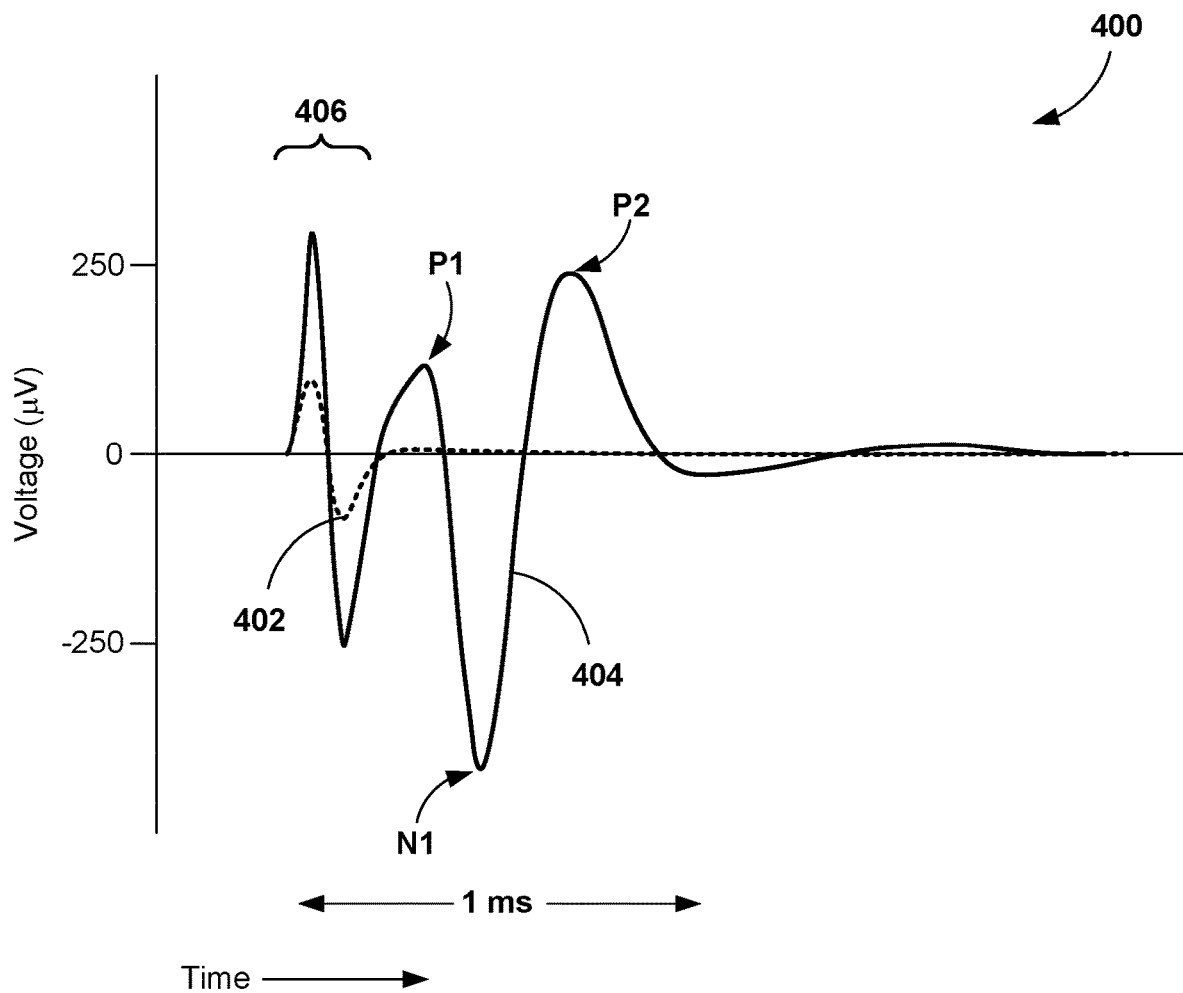
FIG. 4 is a graph of an example ECAP signal sensed from a stimulation pulse.

FIG. 4 is a graph 400 of an example ECAP signals sensed for respective electrical stimulation pulses. As shown in FIG. 3, graph 400 shows example ECAP signal 402 (dotted line) and ECAP signal 404 (solid line). Each of ECAP signals 402 and 404 may be sensed from pulses that were delivered from a guarded cathode and bi-phasic pulses including an interphase interval between each positive and negative phase of the pulse. The guarded cathode of the stimulation electrodes is located at the end of an 8-electrode lead while two sensing electrodes are provided at the other end of the 8-electrode lead. ECAP signal 402 illustrates the voltage amplitude sensed as a result from a sub-threshold stimulation pulse. Peaks 406 of ECAP signal 402 are detected and represent the artifact of the delivered pulse. However, no propagating signal is detected after the artifact in ECAP signal 404 because the pulse was sub-threshold.

In contrast to ECAP signal 402, ECAP signal 404 represents the voltage amplitude detected from a supra-threshold stimulation pulse. Peaks 406 of ECAP signal 404 are detected and represent the artifact of the delivered pulse. After peaks 406, ECAP signal 404 also includes peaks P1, N1, and P2, which are three peaks representative of propagating action potentials from an ECAP. The example duration of the artifact and peaks P1, N1, and P2 is approximately 1 millisecond (ms). When detecting the ECAP of ECAP signal 404, different characteristics may be identified. For example, the characteristic of the ECAP may be the amplitude between N1 and P2. This N1–P2 amplitude can be detected even if the artifact impinges on P1, a relatively large signal, and the N1–P2 amplitude may be minimally affected by electronic drift in the signal. In other examples, the characteristic of the ECAP used to control pulses may be an amplitude of P1, N1, or P2 with respect to neutral or zero voltage. In some examples, the characteristic of the ECAP used to control pulses may be a sum of two or more of peaks P1, N1, or P2. In other examples, the characteristic of ECAP signal 404 may be the area under one or more of peaks P1, N1, and/or P2. In other examples, the characteristic of the ECAP may be a ratio of one of peaks P1, N1, or P2 to another one of the peaks. In some examples, the characteristic of the ECAP may be a slope between two points in the ECAP signal, such as the slope between N1 and P2. In other examples, the characteristic of the ECAP may be the time between two points of the ECAP, such as the time between N1 and P2. The time between two points in the ECAP signal may be referred to as a latency of the ECAP and may indicate the types of fibers being captured by the pulse. ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Other characteristics of the ECAP signal may be used in other examples.

The amplitude of the ECAP signal increases with increased amplitude of the pulse, as long as the pulse amplitude is greater than the threshold such that nerves depolarize and propagate the signal. The target ECAP characteristic (e.g., the target ECAP amplitude) may be determined from the ECAP signal detected from a pulse when pulses are determined to deliver effective therapy to the patient. The ECAP signal thus is representative of the distance between the stimulation electrodes and the nerves appropriate for the stimulation parameter values of the pulses delivered at that time. Therefore, IMD 110 may attempt to use detected changes to the measured ECAP characteristic value to change stimulation pulse parameter values and maintain the target ECAP characteristic value during stimulation pulse delivery. Alternatively, IMD 110 may attempt to prevent undesirable stimulation intensity by decreasing stimulation pulse intensity in response to the ECAP characteristic value exceeding a threshold ECAP characteristic value.

Figure 5:
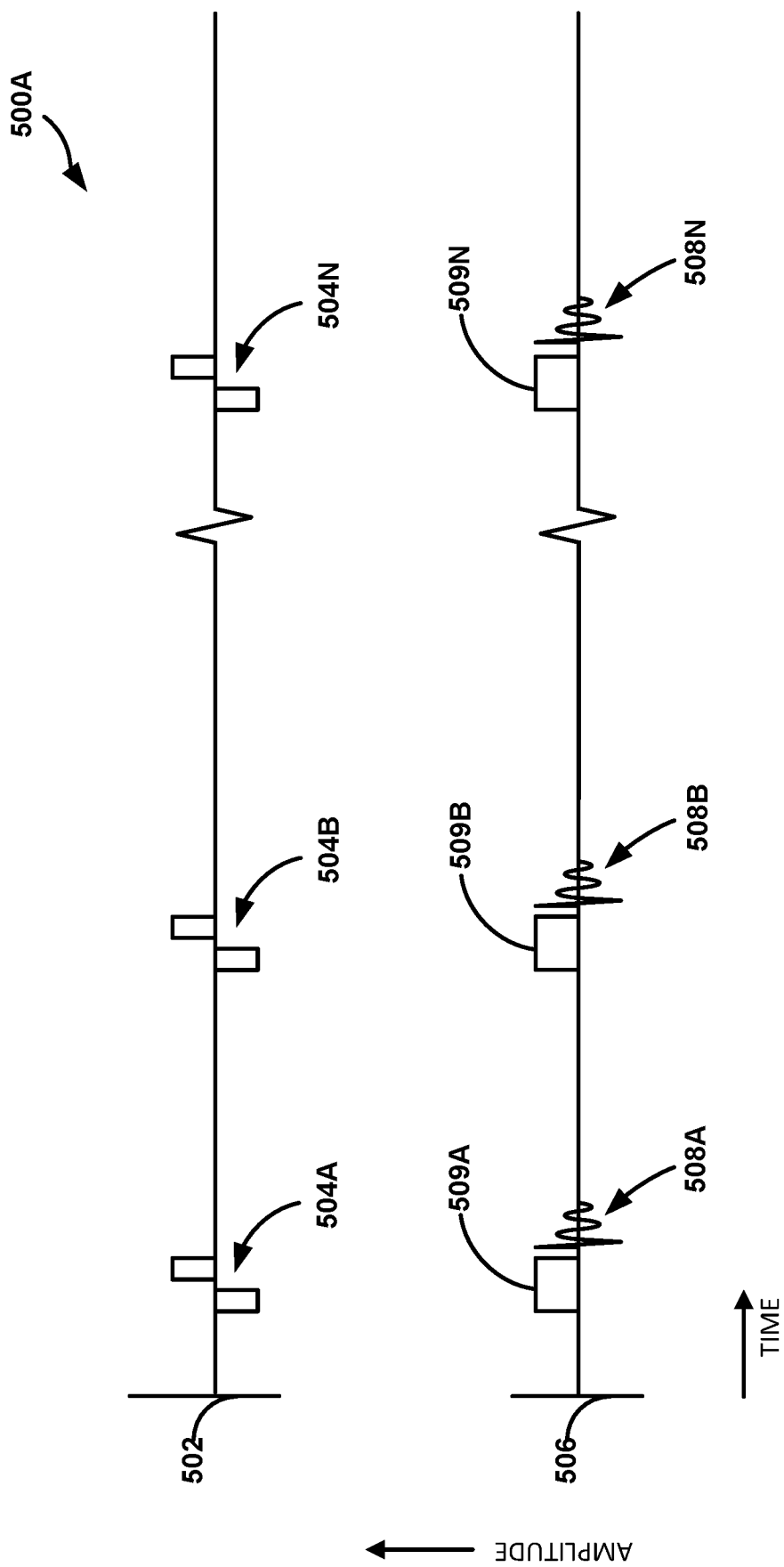
FIG. 5 is a timing diagram illustrating one example of electrical stimulation pulses and respective sensed ECAPs, in accordance with one or more techniques of this disclosure.

FIG. 5 is a timing diagram 500A illustrating one example of electrical stimulation pulses and respective sensed ECAPs, in accordance with one or more techniques of this disclosure. For convenience, FIG. 5 is described with reference to IMD 200 of FIG. 2. As illustrated, timing diagram 500A includes first channel 502, a plurality of control pulses 504A-504N (collectively "control pulses 504"), second channel 506, a plurality of respective ECAPs 508A-508N (collectively "ECAPs 508"), and a plurality of stimulation interference signals 509A-509N (collectively "stimulation interference signals 509"). In the example of FIG. 5, stimulation pulses 504 may or may not contribute to therapy for the patient. In any case, stimulation pulses 504 may elicit respective ECAPs 508 for the purpose of determining relative neural recruitment due to the stimulation pulses 504, which may be reflective as a growth curve specific to the posture state of the patient that was assumed with the ECAPs 508 were sensed.

First channel 502 is a time/voltage (and/or current) graph indicating the voltage (or current) of at least one electrode of electrodes 232, 234. In one example, the stimulation electrodes of first channel 502 may be located on the opposite side of the lead as the sensing electrodes of second channel 506. Stimulation pulses 504 may be electrical pulses delivered to the spinal cord of the patient by at least one of electrodes 232, 234, and stimulation pulses 504 may be balanced biphasic square pulses with an interphase interval. In other words, each of control pulses 504 are shown with a negative phase and a positive phase separated by an interphase interval. For example, a control pulse 504 may have a negative voltage for the same amount of time and amplitude that it has a positive voltage. It is noted that the negative voltage phase may be before or after the positive voltage phase. Stimulation pulses 504 may be delivered according to instructions stored in storage device 212 of IMD 200.

In some examples, each of stimulation pulses 504 may be a part of a sweep of pulses configured to determine a relationship between the stimulation parameter values of the pulses and a characteristic value of the resulting respective ECAPs 508. For example, the relationship may be a growth curve of ECAP voltage amplitude versus pulse current amplitude. In this manner, each of stimulation pulses 504 may differ from each other by a parameter value, such as an iteratively increasing current amplitude. Such sweeps may be performed for each posture state of a plurality of posture states in order to determine the growth curve, gain value, or some characteristic related to ECAPs for that posture state. In one example, stimulation pulses 504 may have a pulse width of less than approximately 300 microseconds (e.g., the total time of the positive phase, the negative phase, and the interphase interval is less than 300 microseconds). In another example, control pulses 504 may have a pulse width of approximately 100 microseconds for each phase of the bi-phasic pulse. In some examples, the pulse width of stimulation pulses 504 may be longer than 300 microseconds, as long as the pulse width does not interfere with the detection of the desired one or more features of the elicited ECAPs 508. As illustrated in FIG. 5, stimulation pulses 504 may be delivered via channel 502. Delivery of stimulation pulses 504 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 506 is a time/voltage (and/or current) graph indicating the voltage (or current) of at least one electrode of electrodes 232, 234. In one example, the electrodes of second channel 506 may be located on the opposite side of the lead as the electrodes of first channel 502. ECAPs 508 may be sensed at electrodes 232, 234 from the spinal cord of the patient in response to stimulation pulses 504. ECAPs 508 are electrical signals which may propagate along a nerve away from the origination of stimulation pulses 504. In one example, ECAPs 508 are sensed by different electrodes than the electrodes used to deliver stimulation pulses 504. As illustrated in FIG. 5, ECAPs 508 may be recorded on second channel 506. In some examples, ECAPs 508 may not be sensed after each stimulation pulse 504.

Stimulation interference signals 509A, 509B, and 509N (e.g., the artifact of the stimulation pulses) may be sensed by leads 230 and may be sensed during the same period of time as the delivery of stimulation pulses 504. Since the interference signals may have a greater amplitude and intensity than ECAPs 508, any ECAPs arriving at IMD 200 during the occurrence of stimulation interference signals 509 may not be adequately sensed by sensing circuitry 206 of IMD 200. However, ECAPs 508 may be sufficiently sensed by sensing circuitry 206 because each ECAP 508, or at least a portion of ECAP 508 that includes one or more desired features of ECAP 508 that is used to detect the posture state and/or as feedback for stimulation pulses 504, falls after the completion of each a stimulation pulse 504. As illustrated in FIG. 5, stimulation interference signals 509 and ECAPs 508 may be recorded on channel 506.

In some examples, IMD 200, for example, may deliver the entire group of stimulation pulses 504 (e.g., a sweep) consecutively and without any other intervening pulses in order to detect ECAPs 508 from which respective characteristic values are determined. IMD 200 may then determine the relationship between the characteristic values from ECAPs 508 and the different parameter values of stimulation pulses 504. In one example, the sweep of pulses 504 may be delivered by IMD 200 during a break in delivery of other types of stimulation pulses.

Figure 6:
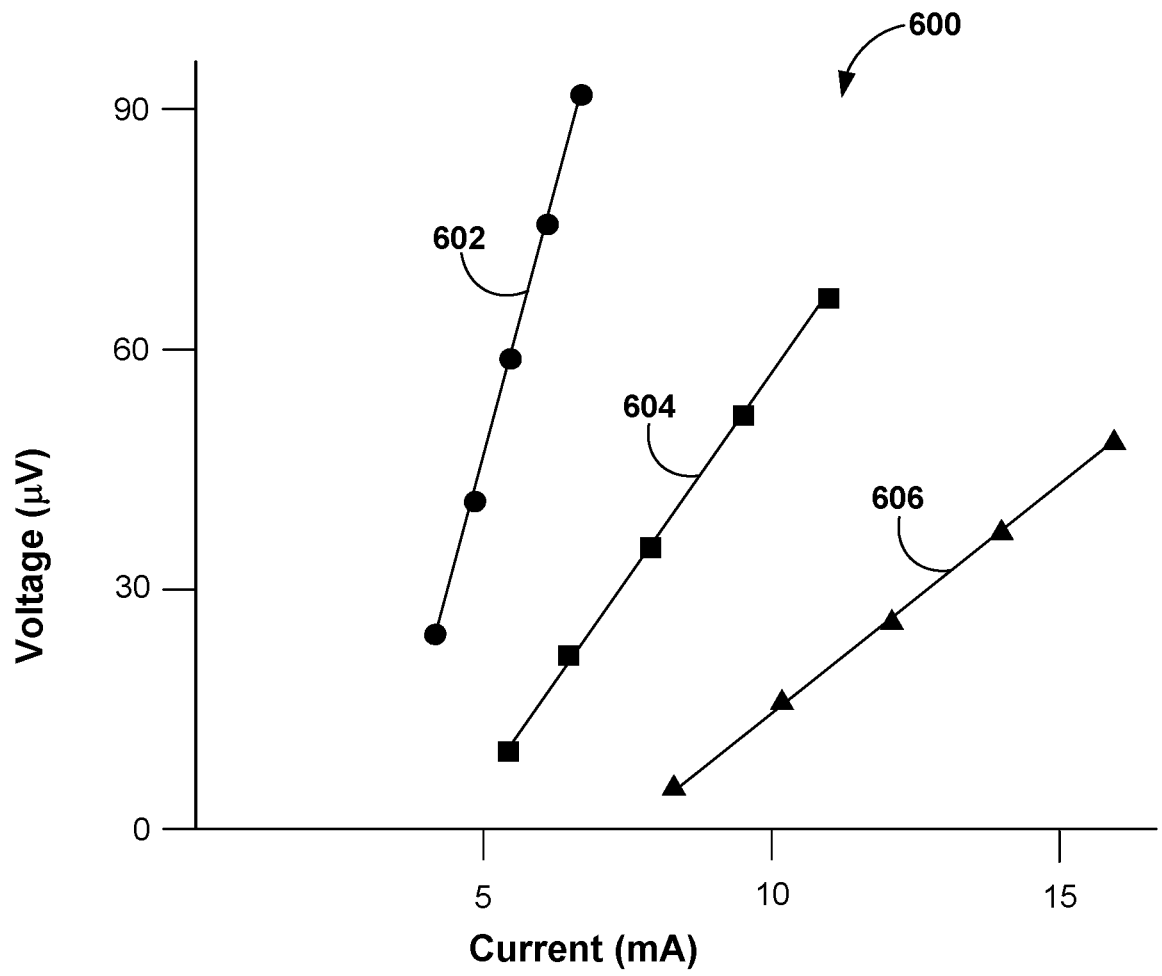
FIG. 6 is a graph of example growth curves derived from sensed ECAPs during respective posture states.

FIG. 6 is a graph 600 of example growth curves 602, 604, and 606 of sensed ECAPs from respective stimulation pulse amplitudes. Graph 600 illustrates example ECAPs shown as dots (growth curve 602), squares (growth curve 604), and triangles (growth curve 606) for respective different current amplitudes of stimulation pulses. ECAPs will sometimes not be generated until the stimulation pulse amplitude reaches a threshold, approximately at 4.5 mA current in the example of FIG. 6. Then, as the current amplitude is increased, the ECAP amplitude also increases approximately linearly. This linear relationship is shown by growth curves 602, 604, 606. Besides growth curves varying based on the posture state of the patient, the slope may vary for each patient based on the type of electrodes implanted, where the electrodes are implanted, the sensitivity of the patient's neurons to stimulation, neurological dysfunction, or other factors.

While a patient is in a given posture state, sensed ECAPs may be detected for stimulation pulses with different current amplitudes. For example, each growth curve 602, 604, and 606 may be for a single posture state, e.g., supine, prone, sitting, standing, or lying on the right side or left side. If a patient changes posture states, the growth curve can also change. When a patient changes posture states, e.g., supine to standing and standing to running, the corresponding growth curve can change as well. For example, growth curve 602 may be associated with a supine posture state, growth curve 604 may be associated with a sitting posture state, and growth curve 606 may be associated with a prone posture state. In some examples, a patient may change posture states, but the same growth curve, or gain value, may apply to the different posture state.

The slope of the growth curves 602, 604, and 606 that linearly increase may indicate the relationship between sensed ECAP amplitudes and pulse amplitudes. In some examples, the gain value used to increase or decrease stimulation parameter values may be inversely proportional to the slope of the growth curve of values of the characteristic of ECAP signals (e.g., an amplitude such as the N1-P2 amplitude or the amplitude of any peak of the ECAP signal) elicited from respective stimulation pulses delivered to the patient and at least partially defined by different values of a stimulation parameter (e.g., current amplitude, voltage amplitude, or pulse width). For example, the gain value for a patient may be used to dynamically adjust pulse amplitude based on the sensed ECAP amplitudes. In some examples, the gain may be approximated for a patient based on historical data for similar patients. In other examples, the system may generate a custom growth curve and gain specific to the patient before starting therapy with the system.

Figure 7:
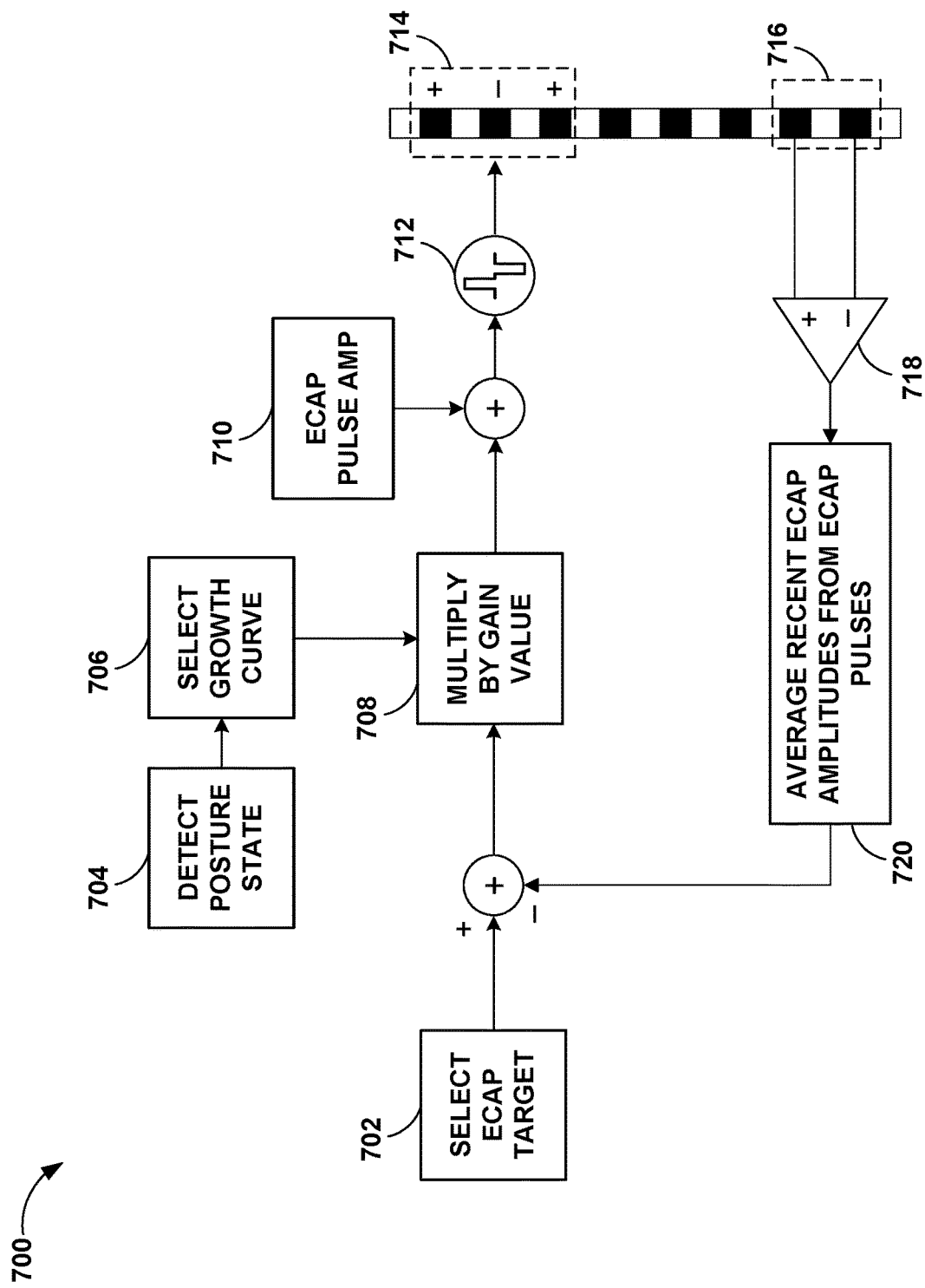
FIG. 7 is a diagram illustrating an example technique for adjusting electrical stimulation therapy.

FIG. 7 is a diagram illustrating an example technique 700 for adjusting stimulation therapy. As shown in the example of FIG. 7, the system, such as IMD 200 or any other device or system described herein, may dynamically adjust pulse amplitude (or other parameter) based on the gain value representing the patient sensitivity to stimulation. Processing circuitry 208 of IMD 200 may control stimulation generation circuitry 204 to deliver a stimulation pulse to a patient. Processing circuitry 208 may then control sensing circuitry 206 to sense an ECAP signal elicited by the pulse and then identify a characteristic of the ECAP signal (e.g., an amplitude of the ECAP signal). Processing circuitry 208 may then determine, based on the characteristic of the ECAP signal and a gain value associated with a growth curve, a stimulation parameter value (e.g., an amplitude, pulse width value, pulse frequency value, and/or slew rate value) that at least partially defines a stimulation pulse. Processing circuitry 208 may then control stimulation generation circuitry 204 to deliver the stimulation pulse according to the determined stimulation pulse.

As shown in FIG. 7, a pulse 712 is delivered to the patient via electrode combination 714, shown as a guarded cathode of three electrodes. The resulting ECAP is sensed by the two electrodes at the opposing end of the lead of electrode combination 716 fed to a differential amplifier 718. For each sensed ECAP, processing circuitry 208 may measure an amplitude of a portion of the ECAP signal, such as the N1–P2 voltage amplitude from the portion of the ECAP signal. Processing circuitry 208 may average the recently measured ECAP amplitudes, such as averaging the most recent, and consecutive, 2, 3, 4, 5, 6, or more ECAP amplitudes. In some examples, the average may be a mean or median value. In some examples, one or more ECAP amplitudes may be ignored from the calculations if the amplitude value is determined to be an error. The measured amplitude (or average measured amplitude) is then subtracted from the selected target ECAP amplitude 702 to generate a differential amplitude. The selected target ECAP amplitude 702 may be determined from an ECAP sensed when the physician or patient initially discovers effective therapy from the stimulation pulses. This target ECAP amplitude 702 may essentially represent a reference distance between the stimulation electrodes and the target neurons (e.g., the spinal cord for the case of SCS).

The differential amplitude is then multiplied by the gain value for the patient to generate a differential value 708. Processing circuitry 208 may detecting patient posture state 704 at varying intervals including, e.g., periodic time intervals, at certain steps of the technique 700, in response to one or more trigger events, or continuously. For example, processing circuitry 208 may be continuously detecting posture state 704 of the patient in order to select a growth curve 706. Once the growth curve is selected 706, processing circuitry 208 may determine a gain value used to generate the differential value 708. In other examples, processing circuitry 208 may select the gain value directly from the detected posture state instead of first selecting the associated growth curve. Processing circuitry 208 may add the differential value to the ECAP pulse amplitude to generate the new, or adjusted, ECAP pulse amplitude 710 that at least partially defines the next pulse 712.

The following formulas may represent the function used to calculate the pulse amplitude of the next pulse 712. Equation 1 below represents an equation for calculating the new current amplitude using a linear function, wherein $A_C$ is the current pulse amplitude, D is the differential amplitude by subtracting the measured amplitude from the target ECAP amplitude, G is a real number for the gain value, and $A_N$ is the new pulse amplitude:

$$A_N = A_C + (D \times G) \tag{1}$$

In this manner, the gain value G may not change for a given input. Alternatively, processing circuitry 208 may calculate the gain value G such that the gain value varies according to one or more inputs or factors, such as posture state. In this manner, for a given input or set of inputs, processing circuitry 208 may change the gain value G. Equation 2 below represents an example linear function for calculating the gain value, wherein M is a multiplier, D is the differential amplitude by subtracting the measured amplitude from the target ECAP amplitude, and G is the gain value:

$$G = M \times D \tag{2}$$

Processing circuitry 208 may use the gain value G calculated in Equation 2 in Equation 1. This would result in Equation 1 being a non-linear function for determining the new current amplitude. According to Equation 2 above, the gain value G may be greater for larger differences between the measured amplitude and the target ECAP amplitude. Thus, gain value G will cause non-linear changes to the current amplitude. In this manner, the rate of change in the current amplitude will be higher for larger differences between the measured amplitude and the target ECAP amplitude and lower for smaller differences between the measured amplitude and the target ECAP amplitude. In other examples, a non-linear function may be used to calculate the gain value G.

The pulse width of the stimulation pulse may be greater than approximately 300 µs and less than approximately 1000 µs. In other examples, the pulse width of the stimulation pulse may be less than approximately 300 µs or greater than 1000 µs. The stimulation pulse may be a monophasic pulse followed a passive recharge phase. However, in other examples, the pulse may be a bi-phasic pulse that includes a positive phase and a negative phase. In some examples, a pulse may be less than 300 µs, but the following passive recharge phase or even an active recharge phase (of a bi-phasic pulse) may still obscure the detectable ECAP signal from that pulse. In other examples, the pulse width of the stimulation pulse may be greater than 300 µs, but some of the ECAP signal may be obscured by the stimulation pulse.

In some examples, depending upon, at least in part, pulse width of the stimulation pulse, IMD 110 may not sufficiently detect an ECAP signal because the stimulation pulse is also detected as an artifact that obscures the ECAP signal. If ECAPs are not adequately recorded, then ECAPs arriving at IMD 110 cannot be used to determine the efficacy of stimulation parameter settings, and electrical stimulation signals cannot be altered according to responsive ECAPs. In some examples, pulse widths may be less than approximately 300 µs, which may increase the amount of each ECAP signal that is detectable. Similarly, high pulse frequencies may interfere with IMD 110 sufficiently detecting ECAP signals. For example, at pulse frequency values (e.g., greater than 1 kHz) that cause IMD 110 to deliver another pulse before an ECAP from the previous pulse can be detected, IMD 110 may not be capable to detecting the ECAP.

Figure 8:
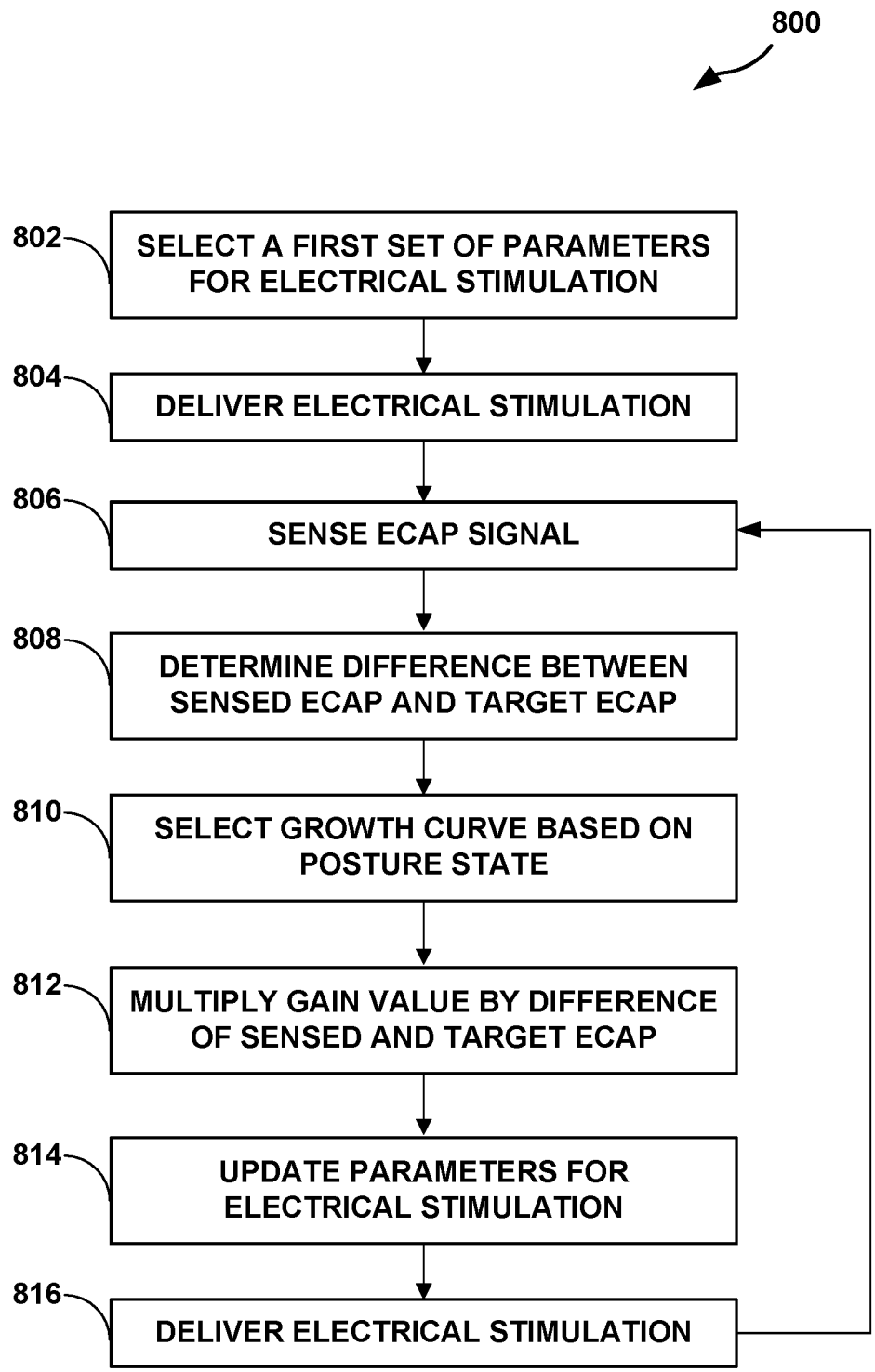
FIG. 8 is a flowchart illustrating an example operation for controlling stimulation, in accordance with one or more techniques of this disclosure.

FIG. 8 is a flow diagram of an example technique for selecting stimulation parameter values. FIG. 8 will be described with processing circuitry 208 of IMD 200, but other devices such as IMD 110 or external programmer 300 may perform similar functions. Besides IMD 200, an external programmer, e.g., external programmer 104, may be used alone or conjunction with one or more other medical devices, e.g., IMD 110 or IMD 200, to determine and set stimulation parameters.

More particularly, FIG. 8 illustrates method 800 in which processing circuitry 208 selects a first set of parameters for electrical stimulation (802). The values for the parameters of electrical stimulation, growth curves, posture states, and target ECAP characteristic (e.g., values of the ECAP indicative of target stimulation intensity) may be initially set/predicted at the clinic but may be set/predicted and/or adjusted at home by patient 102. Once the initial values are set, the example techniques allow for automatic adjustment.

Processing circuitry 208 can be used to control stimulation generator to deliver electrical stimulation (804) according to the first set of parameters for electrical stimulation. Sensing circuitry 206 can sense an ECAP signal (806), and then processing circuitry 208 can receive the ECAP signal. Processing circuitry 208 can then determine and store a value indicative of the ECAP signal in memory 216. In response to sensing the ECAP, processing circuitry 208 can determine the difference between the sensed ECAP and target ECAP (808). Processing circuitry 208 can select a growth curve based on a posture state (810) of the patient.

Detecting patient posture state may be conducted at varying intervals including, e.g., periodic time intervals, at certain predetermined steps of method 800, in response to trigger events such as patient indications of more movement, or continuously. For example, posture state of the patient can be continuously detected in order to select a growth curve based on the currently detected posture state (810). In other examples, processing circuitry 208 may obtain the gain values that are directly associated to respective posture states without the need to first select or obtain a growth curve. The patient posture state data 218 can be stored in memory 216 continuously or non-continuously, including at set time intervals. Once the growth curve is selected, an electrical stimulation amplitude can be determined by using the target ECAP amplitude and the selected growth curve.

The posture state can be continuously updating or a previously detected posture that has been stored in memory 216. The growth curve can be selected using the provided posture state. In some examples, the patient posture state may remain constant for an extended period of time, e.g., on the order of hours. Consequently, the selected growth curve can also remain constant over an extended period of time. A patient can also be consistently changing postures or activity levels, and processing circuitry 208 may continually update the selected growth curve. In some examples, a patient can change posture states that have the same growth.

A gain value can be determined from the slope of the selected growth curve. For example, the gain value may be inversely proportional to the slope of the growth curve. The previously determined difference between the sensed ECAP and the target ECAP can be multiplied by the gain value (812) to determine a new electrical stimulation amplitude. Processing circuitry 208 can then update the parameters for electrical stimulation (814) with the new stimulation amplitude to control delivery of electrical stimulation (816). After delivering electrical stimulation (816), sensing circuitry 206 can sense the ECAP signal (806) and method 800 can proceed to determine whether the parameters for electrical stimulation (814) need to be updated.

FIG. 9 illustrates a graph 900 that includes pulse current amplitude 902, threshold ECAP amplitude 904 (e.g., a type of threshold ECAP characteristic value), and sensed ECAP voltage amplitude 906 as a function of time, in accordance with one or more techniques of this disclosure. For convenience, FIG. 9 is described with respect to IMD 200 of FIG. 2. However, the techniques of FIG. 9 may be performed by different components of IMD 200 than as described herein or by additional or alternative medical devices.

Graph 900 illustrates a relationship between sensed ECAP voltage amplitude and stimulation pulse current amplitude. For example, pulse current amplitude 902 is plotted alongside ECAP voltage amplitude 906 as a function of time, showing how processing circuitry 208 can change stimulation current amplitude relative to ECAP voltage amplitude. In some examples, IMD 200 delivers a plurality of pulses at pulse current amplitude 902. Initially, IMD 200 may deliver a first set of stimulation pulses at current amplitude I. The first set of stimulation pulses may be delivered prior to time T1. In some examples, current amplitude I is less than 25 milliamps (mA) and can be between about 2 mA and about 18 mA. However, current amplitude I may be any current amplitude that IMD 200 can deliver to the patient and appropriate for effective stimulation therapy for the patient.

While delivering the first set pulses, IMD 200 may record ECAP voltage amplitude 906 from ECAPs elicited from the respective pulses. During transient patient movement, ECAP voltage amplitude 906 may increase if pulse current amplitude 902 is held constant and the distance between the electrodes and target nerve decreases. For example, as illustrated in FIG. 9, ECAP voltage amplitude 906 may increase prior to time T1 while stimulation current amplitude is held constant. An increasing ECAP voltage amplitude 906 may indicate that patient 102 is at risk of experiencing transient overstimulation due to the pulses delivered by IMD 200. To prevent patient 102 from experiencing transient overstimulation, IMD 200 may decrease pulse current amplitude 902 in response to ECAP voltage amplitude 906 exceeding the threshold ECAP amplitude 904. For example, if IMD 200 senses an ECAP having an ECAP voltage amplitude 906 meeting or exceeding threshold ECAP amplitude 904, as illustrated in FIG. 9 at time T1, IMD 200 may enter a decrement mode where pulse current amplitude 902 is decreased. In some examples, the threshold ECAP amplitude 904 is greater than 10 microvolts (µV) and less than 100 µV. For example, the threshold ECAP amplitude 904 can be 30 µV. In other examples, the threshold ECAP amplitude 904 is less than or equal to 10 µV or greater than or equal to 100 µV. The exact value of threshold ECAP amplitude 904 may depend on the patient's perception of the delivered stimulation, as well as the spacing between the sensing/stimulation electrodes and the neural tissue, whether or not stimulation intensity is increasing or decreasing, or other factors.

The decrement mode with a plurality of decrement rate settings may, in some cases, be stored in memory 216 of IMD 200 as a part of stimulation parameter settings 220. In the example illustrated in FIG. 9, the decrement mode is executed by IMD 200 over a second set of pulses which occur between time T1 and time T2. In some examples, each decrement in the current amplitude 902 may be determined based on the gain value or growth curve for the currently detected posture state. In some examples, to execute the decrement mode, IMD 200 decreases the pulse current amplitude 902 of each pulse of the second set of pulses according to a first linear function with respect to time. During a period of time in which IMD 200 is operating in the decrement mode (e.g., time interval T2-T1), ECAP voltage amplitude 906 of ECAPs sensed by IMD 200 may be greater than or equal to threshold ECAP amplitude 904.

In the example illustrated in FIG. 9, IMD 200 may sense an ECAP at time T2, where the ECAP has an ECAP voltage amplitude 906 that is less than threshold ECAP amplitude 904. The ECAP sensed at time T2 may, in some cases, be the first ECAP sensed by IMD 200 with a below-threshold amplitude since IMD 200 began the decrement mode at time T1. Based on sensing the ECAP at time T2, IMD 200 may deactivate the decrement mode and activate an increment mode. The increment mode with a plurality of increment rate settings may, in some cases, be stored in memory 216 of IMD 200 as a part of stimulation parameter settings 220. IMD 200 may execute the increment mode over a third set of pulses which occur between time T2 and time T3. In some examples, to execute the increment mode, IMD 200 increases the pulse current amplitude 902 of each pulse of the third set of pulses according to a second linear function with respect to time, back up to the initial current amplitude I that may be predetermined for therapy. In other words, IMD 200 increases each consecutive pulse of the third set of pulses proportionally to an amount of time elapsed since a previous pulse. In other examples, threshold ECAP amplitude 904 may define a lower threshold and an upper threshold, where IMD 200 only enters the decrement mode when ECAP voltage amplitude 906 exceeds the upper threshold, and IMD 200 only enters the increment mode when ECAP voltage amplitude 906 subsequently falls back below the lower threshold. In this manner, IMD 200 may be configured to maintain the current amplitude 902 when ECAP voltage amplitude 906 is between the upper and lower thresholds in order to prevent oscillations in pulse intensity that the patient can perceive if ECAP voltage amplitude 906 is moving up and down around the upper threshold.

When pulse current amplitude 902 returns to current amplitude I (e.g., the predetermined value for stimulation pulses), IMD 200 may deactivate the increment mode and deliver stimulation pulses at constant current amplitudes. By decreasing stimulation in response to ECAP amplitudes exceeding a threshold ECAP characteristic value and subsequently increasing stimulation in response to ECAP amplitudes falling below the threshold, IMD 200 may prevent patient 102 from experiencing transient overstimulation or decrease a severity and/or a time duration of transient overstimulation experienced by patient 102. Although IMD 200 may increase and decrease the amplitudes by linear functions in some examples, IMD 200 may employ non-linear functions in other examples. For example, the gain value may represent a non-linear function in which the increment or decrement changes exponentially or logarithmically according to the difference between the sensed ECAP characteristic value and the threshold ECAP amplitude 904.

The following examples are described herein. Example 1: a system comprising: sensing circuitry configured to sense an evoked compound action potential (ECAP) signal elicited by delivered electrical stimulation; and processing circuitry configured to: control delivery of the electrical stimulation to a patient according to a first value of a stimulation parameter; determine a characteristic value of the ECAP signal detected from the electrical stimulation; receive, from a sensor, a posture state signal representing a posture state of the patient; determine, based on the posture state signal, a gain value for the stimulation parameter; adjust, based on the characteristic value of the ECAP signal and the gain value, the first value of the stimulation parameter to a second value of the stimulation parameter; and control delivery of the electrical stimulation according to the second value of the stimulation parameter.

Example 2 the system of example 1, further comprising stimulation generation circuitry configured to deliver the electrical stimulation to the patient according to a first set of stimulation parameters and a second set of stimulation parameters, wherein the first set of stimulation parameter values comprises the first value of the stimulation parameter and the second set of stimulation parameter values comprises the second value of the stimulation parameter.

Example 3 the system of example 2, wherein the first and second set of stimulation parameters comprise at least one of an amplitude, a pulse width, a pulse frequency, or a pulse shape.

Example 4 the system of any of examples 1 through 3, wherein the processing circuitry is configured to adjust the first value to the second value by one of increasing or decreasing the stimulation parameter of the electrical stimulation based on a growth curve associated with the posture state of the patient.

Example 5 the system of any of examples 1 through 4, wherein the characteristic value is an amplitude of a portion of the ECAP signal, and wherein the processing circuitry is configured to adjust the first value to the second value by: subtracting the amplitude from a target ECAP amplitude value for the patient to generate a differential amplitude; multiplying the differential amplitude by the gain value that at least partially defines the electrical stimulation to generate a differential value; and adding the differential value to a previous amplitude value to generate the second value that at least partially defines the electrical stimulation to be delivered to the patient.

Example 6 the system of example 5, wherein the amplitude of the portion of the ECAP signal comprises a voltage amplitude between an N1 peak and a P2 peak of the ECAP signal.

Example 7 the system of any of examples 1 through 6, wherein the gain value is inversely proportional to a slope of a growth curve defining a relationship of ECAP values to stimulation parameter values for the patient.

Example 8 the system of example 7, wherein the posture state is one posture state of a plurality of posture states, and wherein each posture state comprises a respective growth curve representing the relationship between the ECAP values and stimulation parameter values when the patient occupies that posture state.

Example 9 the system of any of examples 1 through 8, wherein the processing circuitry is configured to adjust the first value to the second value of the stimulation parameter by: comparing the characteristic value of the ECAP signal to a threshold ECAP characteristic value; determining that the characteristic value of the ECAP signal is greater than the threshold ECAP characteristic value; and responsive to determining that the characteristic value of the ECAP signal is greater than the threshold ECAP characteristic value, decreasing the first value to the second value.

Example 10 the system of example 9, wherein the ECAP signal is a first ECAP signal and the characteristic value is a first characteristic value, and wherein the processing circuitry is configured to: determine a second characteristic value of a second ECAP signal elicited from electrical stimulation delivered after sensing the first ECAP signal; determine that the second characteristic value of the second ECAP signal subsequently decreased below the threshold ECAP characteristic value; and responsive to determining that the second characteristic value of the second ECAP signal decreases below the threshold ECAP characteristic value, increase the second value of the stimulation parameter to a third value, the third value being limited to be less than or equal to the first value.

Example 11 the system of example 10, wherein the processing circuitry is configured to increase the second value at a slower rate than the first value was decreased to the second value.

Example 12 the system of any of examples 1 through 11, wherein the processing circuitry is configured to select, based on the posture state signal the gain value from a plurality of gain values associated with respective posture states, wherein the gain value represents at least one of an increment rate or a decrement rate for the stimulation parameter of the electrical stimulation.

Example 13 the system of any of examples 1 through 12, wherein the processing circuitry is configured to: select, based on the posture state signal, a target ECAP characteristic value; compare the characteristic value of the ECAP signal to the threshold ECAP characteristic value; adjust, based on the comparison of the characteristic value of the ECAP signal to the threshold ECAP characteristic value and the gain value, the first value of the stimulation parameter value to the second value of the stimulation parameter.

Example 14 the system of any of examples 1 through 13, wherein the processing circuitry is configured to: determine, from at least the signal representing the posture state of the patient, that the posture state of the patient has changed; and responsive to determining that the posture state has changed, change at least one of an ECAP sensing frequency.

Example 15 the system of any of examples 1 through 14, further comprising an implantable medical device comprising the sensing circuitry and the processing circuitry.

Example 16 a method comprising: sensing, via sensing circuitry, an evoked compound action potential (ECAP) signal elicited by delivered electrical stimulation; controlling, by processing circuitry, delivery of the electrical stimulation to a patient according to a first value of a stimulation parameter; determining, by the processing circuitry, a characteristic value of the ECAP signal detected from the electrical stimulation; receiving, by the processing circuitry and from a sensor, a posture state signal representing a posture state of the patient; determining, by the processing circuitry and based on the posture state signal, a gain value for the stimulation parameter; adjusting, by the processing circuitry and based on the characteristic value of the ECAP signal and the gain value, the first value of the stimulation parameter to a second value of the stimulation parameter; and controlling, by the processing circuitry, delivery of the electrical stimulation according to the second value of the stimulation parameter.

Example 17 the method of example 16, further comprising delivering, by stimulation generation circuitry, the electrical stimulation to the patient according to a first set of stimulation parameters and a second set of stimulation parameters, wherein the first set of stimulation parameter values comprises the first value of the stimulation parameter and the second set of stimulation parameter values comprises the second value of the stimulation parameter.

Example 18 the method of example 17, wherein the first and second set of stimulation parameters comprise at least one of an amplitude, a pulse width, a pulse frequency, or a pulse shape.

Example 19 the method of any of examples 16 through 18, wherein adjusting the first value to the second value comprises one of increasing or decreasing the stimulation parameter of the electrical stimulation based on a growth curve associated with the posture state of the patient.

Example 20 the method of any of examples 16 through 19, wherein the characteristic value is an amplitude of a portion of the ECAP signal, and wherein adjusting the first value to the second value comprises: subtracting the amplitude from a target ECAP amplitude value for the patient to generate a differential amplitude; multiplying the differential amplitude by the gain value that at least partially defines the electrical stimulation to generate a differential value; and adding the differential value to a previous amplitude value to generate the second value that at least partially defines the electrical stimulation to be delivered to the patient.

Example 21 the method of example 20, wherein the amplitude of the portion of the ECAP signal comprises a voltage amplitude between an N1 peak and a P2 peak of the ECAP signal.

Example 22 the method of any of examples 16 through 21, wherein the gain value is inversely proportional to a slope of a growth curve defining a relationship of ECAP values to stimulation parameter values for the patient.

Example 23 the method of example 22, wherein the posture state is one posture state of a plurality of posture states, and wherein each posture state comprises a respective growth curve representing the relationship between the ECAP values and stimulation parameter values when the patient occupies that posture state.

Example 24 the method of any of examples 16 through 23, wherein adjusting the first value to the second value of the stimulation parameter comprises: comparing the characteristic value of the ECAP signal to a threshold ECAP characteristic value; determining that the characteristic value of the ECAP signal is greater than the threshold ECAP characteristic value; and responsive to determining that the characteristic value of the ECAP signal is greater than the threshold ECAP characteristic value, decreasing the first value to the second value.

Example 25 the method of example 24, wherein the ECAP signal is a first ECAP signal and the characteristic value is a first characteristic value, and wherein the method further comprises: determining a second characteristic value of a second ECAP signal elicited from electrical stimulation delivered after sensing the first ECAP signal; determining that the second characteristic value of the second ECAP signal subsequently decreased below the threshold ECAP characteristic value; and responsive to determining that the second characteristic value of the second ECAP signal decreases below the threshold ECAP characteristic value, increasing the second value of the stimulation parameter to a third value, the third value being limited to be less than or equal to the first value.

Example 26 the method of example 25, further comprising increasing the second value at a slower rate than the first value was decreased to the second value.

Example 27 the method of any of examples 16 through 26, further comprising selecting, based on the posture state signal the gain value from a plurality of gain values associated with respective posture states, wherein the gain value represents at least one of an increment rate or a decrement rate for the stimulation parameter of the electrical stimulation.

Example 28 the method of any of examples 16 through 27, further comprising: selecting, based on the posture state signal, a target ECAP characteristic value; comparing the characteristic value of the ECAP signal to the threshold ECAP characteristic value; and adjusting, based on the comparison of the characteristic value of the ECAP signal to the threshold ECAP characteristic value and the gain value, the first value of the stimulation parameter value to the second value of the stimulation parameter.

Example 29 the method of any of examples 16 through 28, further comprising: determining, from at least the signal representing the posture state of the patient, that the posture state of the patient has changed; and responsive to determining that the posture state has changed, changing at least one of an ECAP sensing frequency.

Example 30 the method of any of examples 16 through 29, wherein an implantable medical device comprises the sensing circuitry and the processing circuitry.

Example 31 a computer-readable storage medium comprising instructions that, when executed by processing circuitry, cause the processing circuitry to: control delivery of the electrical stimulation to a patient according to a first value of a stimulation parameter; receive an evoked compound action potential (ECAP) signal elicited by delivered electrical stimulation; determine a characteristic value of the ECAP signal detected from the electrical stimulation; receive, from a sensor, a posture state signal representing a posture state of the patient; determine, based on the posture state signal, a gain value for the stimulation parameter; adjust, based on the characteristic value of the ECAP signal and the gain value, the first value of the stimulation parameter to a second value of the stimulation parameter; and control delivery of the electrical stimulation according to the second value of the stimulation parameter.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A system comprising:
   sensing circuitry configured to sense an evoked compound action potential (ECAP) signal elicited by delivered electrical stimulation; and
   processing circuitry configured to:
      control delivery of the electrical stimulation to a patient according to a first value of a stimulation parameter;
      determine a characteristic value of the ECAP signal detected from the electrical stimulation;
      receive, from a sensor, a posture state signal representing a posture state of the patient, wherein the posture state signal is different from the ECAP signal;
      determine, based on the posture state signal, a gain value to be applied to the stimulation parameter;
      adjust, based on the characteristic value of the ECAP signal and the gain value, the first value of the stimulation parameter to a second value of the stimulation parameter; and
      control delivery of the electrical stimulation according to the second value of the stimulation parameter.

2. The system of claim 1, further comprising stimulation generation circuitry configured to deliver the electrical stimulation to the patient according to a first set of stimulation parameters and a second set of stimulation parameters, wherein the first set of stimulation parameter values comprises the first value of the stimulation parameter and the second set of stimulation parameter values comprises the second value of the stimulation parameter.

3. The system of claim 2, wherein the first and second set of stimulation parameters comprise at least one of an amplitude, a pulse width, a pulse frequency, or a pulse shape.

4. The system of claim 1, wherein the processing circuitry is configured to adjust the first value to the second value by one of increasing or decreasing the stimulation parameter of the electrical stimulation based on a growth curve associated with the posture state of the patient.

5. The system of claim 1, wherein the characteristic value is an amplitude of a portion of the ECAP signal, and wherein the processing circuitry is configured to adjust the first value to the second value by:
   subtracting the amplitude from a target ECAP amplitude value for the patient to generate a differential amplitude;
   multiplying the differential amplitude by the gain value that at least partially defines the electrical stimulation to generate a differential value; and
   adding the differential value to a previous amplitude value to generate the second value that at least partially defines the electrical stimulation to be delivered to the patient.

6. The system of claim 5, wherein the amplitude of the portion of the ECAP signal comprises a voltage amplitude between an N1 peak and a P2 peak of the ECAP signal.

7. The system of claim 1, wherein the gain value is inversely proportional to a slope of a growth curve defining a relationship of ECAP values to stimulation parameter values for the patient.

8. The system of claim 7, wherein the posture state is one posture state of a plurality of posture states, and wherein each posture state comprises a respective growth curve representing the relationship between the ECAP values and stimulation parameter values when the patient occupies that posture state.

9. The system of claim 1, wherein the processing circuitry is configured to adjust the first value to the second value of the stimulation parameter by:
   comparing the characteristic value of the ECAP signal to a threshold ECAP characteristic value;
   determining that the characteristic value of the ECAP signal is greater than the threshold ECAP characteristic value; and
   responsive to determining that the characteristic value of the ECAP signal is greater than the threshold ECAP characteristic value, decreasing the first value to the second value.

10. The system of claim 9, wherein the ECAP signal is a first ECAP signal and the characteristic value is a first characteristic value, and wherein the processing circuitry is configured to:
   determine a second characteristic value of a second ECAP signal elicited from electrical stimulation delivered after sensing the first ECAP signal;
   determine that the second characteristic value of the second ECAP signal subsequently decreased below the threshold ECAP characteristic value; and
   responsive to determining that the second characteristic value of the second ECAP signal decreases below the threshold ECAP characteristic value, increase the second value of the stimulation parameter to a third value, the third value being limited to be less than or equal to the first value.

11. The system of claim 10, wherein the processing circuitry is configured to increase the second value at a slower rate than the first value was decreased to the second value.

12. The system of claim 1, wherein the processing circuitry is configured to select, based on the posture state signal the gain value from a plurality of gain values associated with respective posture states, wherein the gain value represents at least one of an increment rate or a decrement rate for the stimulation parameter of the electrical stimulation.

13. The system of claim 1, wherein the processing circuitry is configured to:
   select, based on the posture state signal, a target ECAP characteristic value;
   compare the characteristic value of the ECAP signal to the threshold ECAP characteristic value;
   adjust, based on the comparison of the characteristic value of the ECAP signal to the threshold ECAP characteristic value and the gain value, the first value of the stimulation parameter value to the second value of the stimulation parameter.

14. The system of claim 1, wherein the processing circuitry is configured to:
   determine, from at least the signal representing the posture state of the patient, that the posture state of the patient has changed; and
   responsive to determining that the posture state has changed, change at least one of an ECAP sensing frequency.

15. The system of claim 1, further comprising an implantable medical device comprising the sensing circuitry and the processing circuitry.

16. A method comprising:
   sensing, via sensing circuitry, an evoked compound action potential (ECAP) signal elicited by delivered electrical stimulation;
   controlling, by processing circuitry, delivery of the electrical stimulation to a patient according to a first value of a stimulation parameter;
   determining, by the processing circuitry, a characteristic value of the ECAP signal detected from the electrical stimulation;
   receiving, by the processing circuitry and from a sensor, a posture state signal representing a posture state of the patient, wherein the posture state signal is different from the ECAP signal;
   determining, by the processing circuitry and based on the posture state signal, a gain value for to be applied to the stimulation parameter;
   adjusting, by the processing circuitry and based on the characteristic value of the ECAP signal and the gain value, the first value of the stimulation parameter to a second value of the stimulation parameter; and
   controlling, by the processing circuitry, delivery of the electrical stimulation according to the second value of the stimulation parameter.

17. The method of claim 16, further comprising delivering, by stimulation generation circuitry, the electrical stimulation to the patient according to a first set of stimulation parameters and a second set of stimulation parameters, wherein the first set of stimulation parameter values comprises the first value of the stimulation parameter and the second set of stimulation parameter values comprises the second value of the stimulation parameter.

18. The method of claim 17, wherein the first and second set of stimulation parameters comprise at least one of an amplitude, a pulse width, a pulse frequency, or a pulse shape.

19. The method of claim 16, wherein adjusting the first value to the second value comprises one of increasing or decreasing the stimulation parameter of the electrical stimulation based on a growth curve associated with the posture state of the patient.

20. The method of claim 16, wherein the characteristic value is an amplitude of a portion of the ECAP signal, and wherein adjusting the first value to the second value comprises:
   subtracting the amplitude from a target ECAP amplitude value for the patient to generate a differential amplitude;
   multiplying the differential amplitude by the gain value that at least partially defines the electrical stimulation to generate a differential value; and
   adding the differential value to a previous amplitude value to generate the second value that at least partially defines the electrical stimulation to be delivered to the patient.

21. The method of claim 20, wherein the amplitude of the portion of the ECAP signal comprises a voltage amplitude between an N1 peak and a P2 peak of the ECAP signal.

22. The method of claim 16, wherein the gain value is inversely proportional to a slope of a growth curve defining a relationship of ECAP values to stimulation parameter values for the patient.

23. The method of claim 22, wherein the posture state is one posture state of a plurality of posture states, and wherein each posture state comprises a respective growth curve representing the relationship between the ECAP values and stimulation parameter values when the patient occupies that posture state.

24. The method of claim 16, wherein adjusting the first value to the second value of the stimulation parameter comprises:
   comparing the characteristic value of the ECAP signal to a threshold ECAP characteristic value;
   determining that the characteristic value of the ECAP signal is greater than the threshold ECAP characteristic value; and
   responsive to determining that the characteristic value of the ECAP signal is greater than the threshold ECAP characteristic value, decreasing the first value to the second value.

25. The method of claim 24, wherein the ECAP signal is a first ECAP signal and the characteristic value is a first characteristic value, and wherein the method further comprises:
   determining a second characteristic value of a second ECAP signal elicited from electrical stimulation delivered after sensing the first ECAP signal;
   determining that the second characteristic value of the second ECAP signal subsequently decreased below the threshold ECAP characteristic value; and
   responsive to determining that the second characteristic value of the second ECAP signal decreases below the threshold ECAP characteristic value, increasing the second value of the stimulation parameter to a third value, the third value being limited to be less than or equal to the first value.

26. The method of claim 25, further comprising increasing the second value at a slower rate than the first value was decreased to the second value.

27. The method of claim 16, further comprising selecting, based on the posture state signal the gain value from a plurality of gain values associated with respective posture states, wherein the gain value represents at least one of an increment rate or a decrement rate for the stimulation parameter of the electrical stimulation.

28. The method of claim 16, further comprising:
   selecting, based on the posture state signal, a target ECAP characteristic value;
   comparing the characteristic value of the ECAP signal to the threshold ECAP characteristic value; and
   adjusting, based on the comparison of the characteristic value of the ECAP signal to the threshold ECAP characteristic value and the gain value, the first value of the stimulation parameter value to the second value of the stimulation parameter.

29. The method of claim 16, further comprising:
  determining, from at least the signal representing the posture state of the patient, that the posture state of the patient has changed; and
  responsive to determining that the posture state has changed, changing at least one of an ECAP sensing frequency.

30. The method of claim 16, wherein an implantable medical device comprises the sensing circuitry and the processing circuitry.

31. A non-transitory computer-readable storage medium comprising instructions that, when executed by processing circuitry, cause the processing circuitry to:
  control delivery of the electrical stimulation to a patient according to a first value of a stimulation parameter;
  receive an evoked compound action potential (ECAP) signal elicited by delivered electrical stimulation;
  determine a characteristic value of the ECAP signal detected from the electrical stimulation;
  receive, from a sensor, a posture state signal representing a posture state of the patient, wherein the posture state signal is different from the ECAP signal;
  determine, based on the posture state signal, a gain value for to be applied to the stimulation parameter;
  adjust, based on the characteristic value of the ECAP signal and the gain value, the first value of the stimulation parameter to a second value of the stimulation parameter; and
  control delivery of the electrical stimulation according to the second value of the stimulation parameter.

32. The system of claim 1, wherein the sensor comprises an accelerometer that generates the posture state signal representing the posture state of the patient.

* * * * *

UNITED STATES PATENT AND TRADEMARK OFFICE
CERTIFICATE OF CORRECTION

PATENT NO. : 12,064,631 B2
APPLICATION NO. : 17/100384
DATED : August 20, 2024
INVENTOR(S) : Pulliam et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 599 days.

Signed and Sealed this
Eleventh Day of March, 2025

Coke Morgan Stewart
*Acting Director of the United States Patent and Trademark Office*